United States Patent
May et al.

(10) Patent No.: US 11,857,530 B2
(45) Date of Patent: Jan. 2, 2024

(54) CANNABINOID FORMULATIONS

(71) Applicant: Endocanna Health, Inc., Encino, CA (US)

(72) Inventors: Len May, Encino, CA (US); Eric Kaufman, Encino, CA (US)

(73) Assignee: ENDOCANNA HEALTH, INC., Burbank, CA (US)

( * ) Notice: Subject to any disclaimer, the term of this patent is extended or adjusted under 35 U.S.C. 154(b) by 202 days.

(21) Appl. No.: 16/760,159

(22) PCT Filed: Oct. 30, 2018

(86) PCT No.: PCT/US2018/058199
§ 371 (c)(1),
(2) Date: Apr. 29, 2020

(87) PCT Pub. No.: WO2019/089583
PCT Pub. Date: May 9, 2019

(65) Prior Publication Data
US 2020/0253921 A1 Aug. 13, 2020

Related U.S. Application Data

(60) Provisional application No. 62/721,294, filed on Aug. 22, 2018, provisional application No. 62/680,885, filed on Jun. 5, 2018, provisional application No. 62/707,300, filed on Oct. 30, 2017.

(51) Int. Cl.
| | | |
|---|---|---|
| *A61K 31/352* | (2006.01) | |
| *A61K 31/015* | (2006.01) | |
| *A61K 31/05* | (2006.01) | |
| *G16H 10/40* | (2018.01) | |
| *G16H 10/60* | (2018.01) | |
| *G16H 15/00* | (2018.01) | |
| *G16H 50/70* | (2018.01) | |
| *G16H 50/20* | (2018.01) | |
| *G16H 70/40* | (2018.01) | |
| *G16H 20/10* | (2018.01) | |
| *G16B 20/20* | (2019.01) | |
| *G06F 3/0484* | (2022.01) | |
| *A61K 45/06* | (2006.01) | |

(52) U.S. Cl.
CPC .......... *A61K 31/352* (2013.01); *A61K 31/015* (2013.01); *A61K 31/05* (2013.01); *G06F 3/0484* (2013.01); *G16B 20/20* (2019.02); *G16H 10/40* (2018.01); *G16H 10/60* (2018.01); *G16H 15/00* (2018.01); *G16H 20/10* (2018.01); *G16H 50/20* (2018.01); *G16H 50/70* (2018.01); *G16H 70/40* (2018.01); *A61K 45/06* (2013.01)

(58) Field of Classification Search
CPC ..... A61K 31/352; A61K 31/015; A61K 31/05
See application file for complete search history.

(56) References Cited

U.S. PATENT DOCUMENTS

| | | |
|---|---|---|
| 2011/0064720 A1 | 3/2011 | Amato |
| 2014/0295040 A1* | 10/2014 | Milici ............... A23L 33/22 426/330.2 |
| 2016/0250270 A1 | 9/2016 | Wendschuh et al. |
| 2016/0279073 A1 | 9/2016 | Donsky et al. |
| 2017/0172977 A1 | 6/2017 | Kleidon et al. |

FOREIGN PATENT DOCUMENTS

| | | |
|---|---|---|
| WO | 2014/100231 A1 | 6/2014 |
| WO | 2017/158539 A1 | 9/2017 |
| WO | 2017/182950 A1 | 10/2017 |

OTHER PUBLICATIONS

PCT International Search Report and Written Opinion, PCT International Application No. PCT/US2018/058199, dated Jan. 7, 2019, 23 pages.
Crippa, Jose Alexandre S. et al. "Neural Basis of Anxiolytic Effects of Cannabidiol (CBD) in Generalized Social Anxiety Disorder: A Preliminary Report", Journal of Psychopharmacology vol. 25, Jan. 2011, pp. 121-130.
EP Partial Supplementary Search Report, EP Application No. 18872736.6, dated Jul. 27, 2021, 16 pages.

* cited by examiner

*Primary Examiner* — Sahar Javanmard
(74) *Attorney, Agent, or Firm* — McDonnell Boehnen Hulbert & Berghoff LLP

(57) ABSTRACT

The disclosure is directed to formulations comprising cannabinoids. More particularly, the cannabinoid formulations can be designed to align with an individual's genotype based on a defined list of polymorphisms.

10 Claims, No Drawings

CANNABINOID FORMULATIONS

RELATED APPLICATIONS

This application claims the benefit of U.S. Provisional Application No. 62/707,300, filed Oct. 30, 2017, U.S. Provisional Application No. 62/680,885, filed Jun. 5, 2018, and U.S. Provisional Application No. 62/721,294, filed Aug. 22, 2018, the disclosures of each of which are explicitly incorporated by reference herein in their entirety.

FIELD OF THE INVENTION

The disclosure is directed to cannabinoid formulations. More particularly, the cannabinoid formulations can be designed to align with an individual's genotype based on a defined list of polymorphisms.

BACKGROUND OF THE INVENTION

Medical use of *cannabis* and associated phytocannabinoids is becoming widely accepted in the United States and Canada as an alternative form of medicine. Many states have legalized its use for qualified medical conditions such as chronic pain, epilepsy, sleep disorders, anxiety, cancer, glaucoma, nausea, ALS, Alzheimer's disease, Crohn's disease, Post-traumatic Stress Disorder (PTSD), arthritis, fibromyalgia, and others. Every individual has an endocannabinoid system comprised of chemical receptors in the brain, immune system and central nervous system (for example, cannabinoid receptors CB1 and CB2).

Single nucleotide polymorphisms (SNPs) are stable genetic markers throughout the human genome, which can be tested for their association with various disease traits. These markers can also be associated with various traits that can determine an individual's sensitivity to certain compounds present in *cannabis* such as cannabinoids, terpenes, nitrogenous compounds, flavonoids, non-cannabinoid phenols and other miscellaneous chemical constituents. These endogenous endocannabinoid SNP markers can be tested in a patient and used as biomarkers that may predict how a patient will react or respond to the metabolism of compounds such as delta-9-THC, cannabidiol, other cannabinoids, and terpinoids found in *cannabis*. Furthermore, these biomarkers may suggest the best modality of treatment based on an individual's genetic profile and presence of specific enzymes or lack thereof that may result in negative side-effects from these compounds.

The invention provides cannabinoid formulations that are designed to align with an individual's genotype based on a defined list of polymorphisms.

SUMMARY OF THE INVENTION

It is against the above background that the present invention provides certain advantages and advancements over the prior art. This disclosure relates to cannabinoid formulations that are designed to align with an individual's genotype based on a defined list of polymorphisms, and provide more reliable methods for achieving consistent and predictable results. The inventors have found that specific phytocannabinoid ratios, secreted plant based oils, and terpene profiles align with a subject's genotype.

These and other features and advantages of the present invention will be more fully understood from the following detailed description taken together with the accompanying claims. It is noted that the scope of the claims is defined by the recitations therein and not by the specific discussion of features and advantages set forth in the present description.

In an aspect, the disclosure provides formulations comprising a cannabidiol (CBD) and a tetrahydrocannabinol (THC), wherein the formulation has a CBD:THC ratio from about 50:1 to about 1:50. In some embodiments, the formulations further comprise at least one terpene selected from alpha-bisabolol, alpha-phellandrene, alpha-pinene, alpha-terpinene, beta-caryophyllene, beta-ocimene, beta-pinene, bisabolol, borneol, cadinene, camphene, camphor, cannabinoids, carene, caryophyllene oxide, cedrene, citral, citronellol, curcuminoids, cymene, delta-3-carene, eucalyptol, eugenol, fenchol, gamma-terpinene, geraniol, geranyl acetate, ginkgolides, guaiol, humulene, isobomeol, isopulegol, limonene, linalool, menthol, myrcene, nerol, nerolidol, ocimene, para-cymene, phytol, pinene, pulegone, sabinene, salvinorin, terpineol, terpinolene, theramine and valencene. In certain embodiments, the at least one terpene comprises a primary terpene and a secondary terpene. In some embodiments, the formulations comprise less than about 25%, about 20%, about 15%, about 10%, about 5%, about 4%, about 3%, about 2%, or about 1% terpenes.

In some embodiments, the formulation comprises a primary terpene that is myrcene and a secondary terpene that is linalool, and has a CBD:THC ratio of about 1:1 to about 1:5. In certain embodiments, the formulation comprises 5% myrcene and 3% linalool, and has a CBD:THC ratio of 1:1. In an embodiment, the formulation comprises 5% myrcene, 3% linalool, CBD, and is essentially free of THC.

In some embodiments, the formulation comprises a primary terpene that is pinene and a secondary terpene that is terpineol, and has a CBD:THC ratio of about 20:1 to about 1:1. In certain embodiments, the formulation comprises 5% pinene and 3% terpineol, and has a CBD:THC ratio of 4:1. In an embodiment, the formulation comprises 5% pinene, 3% terpineol, CBD, and is essentially free of THC.

In some embodiments, the formulation comprises a primary terpene that is limonene and a secondary terpene that is linalool, and has a CBD:THC ratio of about 20:1 to about 2:1. In certain embodiments, the formulation comprises 5% limonene and 3% linalool, and has a CBD:THC ratio of 1:1. In an embodiment, the formulation comprises 5% limonene, 3% linalool, CBD, and is essentially free of THC.

In some embodiments, the formulation comprises a primary terpene that is limonene and a secondary terpene that is pinene, and has a CBD:THC ratio of about 1:1 to about 1:20. In certain embodiments, the formulation comprises 5% limonene and 3% pinene, and has a CBD:THC ratio of 1:2. In an embodiment, the formulation comprises 5% limonene, 3% pinene, CBD, and is essentially free of THC.

In some embodiments, the formulation comprises a primary terpene that is linalool and a secondary terpene that is borneol, and has a CBD:THC ratio of about 18:1 to about 4:1. In certain embodiments, the formulation comprises 5% linalool and 1% borneol, and has a CBD:THC ratio of 4:1. In an embodiment, the formulation comprises 5% linalool, 1% borneol, CBD, and is essentially free of THC.

In some embodiments, the formulation comprises a primary terpene that is beta-caryophyllene and a secondary terpene that is humulene, and has a CBD:THC ratio of about 1:1 to about 1:10. In certain embodiments, the formulation comprises 5% beta-caryophyllene and 3% humulene, and has a CBD:THC ratio of 1:1. In an embodiment, the formulation comprises 5% beta-caryophyllene, 3% humulene, CBD, and is essentially free of THC.

In some embodiments, the formulation comprises a primary terpene that is beta-caryophyllene and a secondary terpene that is myrcene, and has a CBD:THC ratio of about 1:1 to about 1:6. In certain embodiments, the formulation comprises 5% beta-caryophyllene and 5% myrcene, and has a CBD:THC ratio of 1:2. In an embodiment, the formulation comprises 5% beta-caryophyllene, 5% myrcene, CBD, and is essentially free of THC.

In some embodiments, the formulations comprise less than about 0.03% THC. In certain embodiments, the formulations are essentially free of THC.

In some embodiments, the formulation comprises a CBD:THC ratio of about 1:1 to about 1:3. In certain embodiments, the formulation comprises branched-chain amino acids, L-glutamine, piperine, magnesium stearate, MCC, and silicon dioxide, wherein the CBD:THC ratio is about 1:2. In an embodiment, the formulation comprises branched-chain amino acids, L-glutamine, piperine, magnesium stearate, MCC, silicon dioxide, CBD, and is essentially free of THC.

In some embodiments, the formulations as disclosed herein comprise from about 0.1 to about 100 mg/mL of the CBD. In other embodiments, the formulations as described herein comprise from about 0.1 to about 100 mg/mL of the THC.

In some embodiments, the formulations as described herein are formulated for buccal, dermal, intranasal, intravenous, nasal, ophthalmic, oral, sublingual, topical, or transdermal administration.

In some embodiments, the formulations as described herein further comprise cannabigerol (CBG), cannabinol (CBN), cannabidvarin (CBDV), cannabidiolic acid (CBDA), tetrahydrocannabinolic acid (THCA), or tetrahydrocannabivarin (THCV).

In some embodiments, the formulations as described herein further comprise black pepper, branched-chain amino acids (BCAA), cayenne, cedarwood, chamomile, coconut oil, geranium, ginger, ginger oil, glutamine, guava, juniper berry, lavender, lemon, lemon oil, lemongrass, lime, lime oil, orange, orange oil, mango, marjoram, menthol, mint, mint oil, peppermint, peppermint oil, piperine, geranium, rosemary, sandalwood, or tangerine.

In another aspect, the disclosure provides methods for treating a sleeping disorder, stress or depression, inflammation, anxiety, or for improving wellness or recovery comprising administering a pharmaceutically effective amount of any of the formulations as disclosed herein.

In yet another aspect, the disclosure provides methods for treating a subject comprising:
(a) determining the subject's DNA genotype;
(b) matching the subject with any of the formulations as disclosed herein based on the subject's DNA genotype; and
(c) administering a pharmaceutically effective amount of any of the formulations as disclosed herein to the subject.

In some embodiments of the method of treating, the subject's DNA genotype is assessed to identify one or more single nucleotide polymorphisms (SNPs) and a pharmaceutically effective amount of any of the formulations as disclosed herein is administered to the subject as disclosed in Table 10.

DETAILED DESCRIPTION OF THE INVENTION

The disclosure involves compositions comprising selective formulations comprising cannabinoid molecules and terpenes that can be extracted from *cannabis* plants. The cannabinoid formulations as disclosed herein are designed to selectively affect a subject based on the subject's personal genetics, which results in important insights into the subject's optimal *cannabis* experience. Thus, the formulations can be personalized to comprise specific cannabinoid ratios and terpene profiles that help the subject achieve optimum results. The formulations disclosed herein provide numerous benefits and advantages, and allow a wide range of prevention, treatment, and management options for subjects based on their specific genotype.

All publications, patents and patent applications cited herein are hereby expressly incorporated by reference for all purposes.

Before describing the present invention in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the term "and/or" is utilized to describe multiple components in combination or exclusive of one another. For example, "x, y, and/or z" can refer to "x" alone, "y" alone, "z" alone, "x, y, and z," "(x and y) or z," "x and (y or z)," or "x or y or z."

As used herein, the terms "polynucleotide," "nucleotide," "oligonucleotide," and "nucleic acid" can be used interchangeably to refer to nucleic acid comprising DNA, RNA, derivatives thereof, or combinations thereof.

In one aspect, the disclosure provides formulations comprising a cannabidiol (CBD) and a tetrahydrocannabinol (THC), wherein the formulation has a CBD:THC ratio from about 50:1 to about 1:50. In some embodiments, the CBD:THC ratio of the formulations described herein will be greater than or equal to 50:1, 45:1, 40:1, 35:1, 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3: 1:4, 1:5, 1:6, 1:7, 1:8, 1:9, 1:10, 1:11, 1:12: 1:13, 1:14, 1:15, 1:16, 1:17, 1:18, 1:19, 1:20, 1:25, 1:30, 1:30, 1:35, 1:40, 1:45, 1:50, or lower. In certain embodiments, the formulations as disclosed herein do not contain THC, or are essentially free of THC.

In some embodiments, the formulations further comprise at least one terpene. Examples of terpenes include, but are not limited to: alpha-bisabolol, alpha-phellandrene, alpha-pinene, alpha-terpinene, beta-caryophyllene, beta-ocimene, beta-pinene, bisabolol, borneol, cadinene, camphene, camphor, cannabinoids, carene, caryophyllene oxide, cedrene, citral, citronellol, curcuminoids, cymene, delta-3-carene, eucalyptol, eugenol, fenchol, gamma-terpinene, geraniol, geranyl acetate, ginkgolides, guaiol, humulene, isobomeol, isopulegol, limonene, linalool, menthol, myrcene, nerol, nerolidol, ocimene, para-cymene, phytol, pinene, pulegone, sabinene, salvinorin, terpineol, terpinolene, theramine and valencene. In certain embodiments, the formulations comprise at least a primary terpene and a secondary terpene.

As used herein, the term "cannabinoid" refers to the chemical compounds found in *cannabis* that mimic and supplement body biochemicals—endocannabinoids—that interact and ultimately control receptors found in every cell in the human body. Cannabinoids in *Cannabis*, especially THC and CBD, modulate the receptors CB1 and CB2, which are involved in the function of nearly every body system, disease and condition. The cannabinoid receptor type 1 (CB1 receptor), is primarily expressed in the brain, and is encoded by the gene CNR1. Mutations of this gene alter the endocannabinoid system and response to THC. Genetic variants are associated with an increased risk of anxiety, onset of paranoia, and addiction. The cannabinoid receptor type 2 (CB2 receptor), is encoded by the gene CNR2, and is primarily expressed in the periphery, but may also be expressed in the brain following neuroinflammatory conditions. Mutations of this gene are associated with difficulty in controlling pain, including neuropathic pain and diabetic neuropathy.

Over 600 cannabinoids have been identified, but only Δ-8 tetrahydrocannabinol (Δ-8 THC), Δ-9 tetrahydrocannabinol (Δ-9 THC), and hydroxyl metabolites of those are psychoactive. Cannabinoids commonly found in *cannabis* include, but are not limited to, CBC, CBCV, CBD, CBDA, CBDV, CBG, CBGV, CBL, CBN, CBV, THC, THCA, THCV. The amount of each cannabinoid depends on the strain.

In some embodiments, the formulations as disclosed herein can further comprise cannabigerol (CBG), cannabinol (CBN), cannabidvarin (CBDV), cannabidiolic acid (CBDA), tetrahydrocannabinolic acid (THCA), or tetrahydrocannabivarin (THCV). In certain embodiments, the formulations as disclosed herein can comprise one or more of CBC, CBCV, CBD, CBDA, CBDV, CBG, CBGV, CBL, CBN, CBV, THC, THCA, and THCV.

Cannabichromene (CBC) is non-psychoactive and does not affect the psychoactivity of THC. CBC is typically more common in tropical *cannabis* varieties. Effects include anti-inflammatory and analgesic.

Cannabichromevarin (CBCV) is a propyl cannabinoid, which means it has a propyl chain in its molecular structure. Instead of having a pentyl chain like its counterpart, cannabichromene (CBC), it branches off to have a propyl chain. CBCV could relieve seizures in children and infants.

Cannabidiol (CBD) is a non-psychoactive compound in *cannabis* that has significant medical benefits. In the general population, high doses of CBD is expected to produce sedative and calming effects, while lower CBD doses have been shown to enhance mood.

Cannabidiolic acid (CBDA) is a cannabinoid found in raw *cannabis*, meaning fresh flowers and leaves that are unheated. CBDA is decarboxylated to CBD with heat and light exposure.

Cannabidivarin (CBDV) is a non-psychoactive cannabinoid known for its anticonvulsant effects. Both cannabidivarin (CBDV) and cannabidiol (CBD) activate and desensitize transient receptor potential vanilloid 1 (TRPV1) channels in vitro and thus have a potential for the treatment of neuronal hyperexcitability.

Cannabigerol (CBG) is a non-psychoactive cannabinoid found in the fresh *cannabis* plant. CBG is made by the decarboxylation of CBGA. CBG is a highly potent agonist for u2 adrenoceptor and a blocker of serotonin 5-HT1A receptor. This activity can decrease anxiety and muscle tension.

Cannabigerovarin (CBGV) is the propyl homologue of cannabigerol (CBG). CBGV is a potent inhibitor of LPI-induced GPR55 signaling. CBGV has been shown to be holding great potential for treating cancer. CBGV was shown to be cytostatic in leukemic cells and caused a simultaneous arrest at all phases of the cell cycle.

Cannabicyclol (CBL) is a non-psychotomimetic cannabinoid found in the *Cannabis* species. CBL is a degradative product like cannabinol. Light converts cannabichromene to CBL.

Cannabinol (CBN) is a non-psychoactive cannabinoid found in fresh *cannabis*, usually in low amounts. Unlike other cannabinoids, CBN does not stem from cannabigerol (CBG). CBN is formed by decarboxylation of CBNA. CBN has exhibited pain relief properties.

Cannabivarin (CBV), also known as cannabivarol, is a non-psychoactive cannabinoid found in minor amounts in the hemp plant *Cannabis sativa*. It is an analog of cannabinol (CBN) with the side chain shortened by two methylene bridges (—CH2-). CBV is an oxidation product of tetrahydrocannabivarin (THCV, THV).

Tetrahydrocannabinol (THC) is the most well-known and most abundantly available cannabinoid in *cannabis* plants. THC is also the component in *cannabis* that is responsible for the psychoactive effects, or the "high." Also known as delta-9-tetracannabinol, it was first isolated in 1964.

Tetrahydrocannabinolic acid (THCA) is a non-psychoactive cannabinoid found in raw *cannabis*, meaning fresh flowers and leaves that are unheated. THCA is decarboxylated to psychoactive THC with heat and light exposure. This decarboxylation is what happens when one vaporizes or smokes flower.

Tetrahydrocannabivarin (THCV) is a non-psychoactive cannabinoid in *cannabis*, and a precursor of THC and CBD. THCV acts like a CB1 antagonist, and may aid in weight reduction. THCV has also shown to be useful for glycemic control in patients with type 2 diabetes.

As used herein the terms "terpene" and "terpinoid" can be used interchangeably and refer to a large and diverse class of organic compounds, produced by a variety of plants. They are often strong smelling and may have a protective function. Terpenes are known to play a role in traditional herbal remedies and are under investigation for antibacterial, antineoplastic, and other pharmaceutical functions. Terpenes can act synergistically with cannabinoids to provide a therapeutic effect. Terpene can be acyclic, monocyclic, bicyclic, or multicyclic, and can be derived biosynthetically from units of isoprene, which has the molecular formula $C_5H_8$. The basic molecular formulae of terpenes are multiples of that, $(C_5H_8)_n$ where n is the number of linked isoprene units. The isoprene units may be linked together "head to tail" to form linear chains or they may be arranged to form rings. Non-limiting examples of terpenes include hemiterpenes, monoterpenes, sesquiterpenes, diterpenes, sesterterpenes, triterpenes, sesquarterpenes, tetraterpenes, polyterpenes, and norisoprenoids. Examples of terpenes can include: alpha-bisabolol, alpha-phellandrene, alpha-pinene, alpha-terpinene, beta-caryophyllene, beta-ocimene, beta-pinene, bisabolol, borneol, cadinene, camphene, camphor, cannabinoids, careen, caryophyllene oxide, citral, citronellol, curcuminoids, delta-3-carene, eucalyptol, eugenol, fenchol, gamma-terpinene, geraniol, ginkgolides, humulene, limonene, linalool, menthol, myrcene, nerol, nerolidol, ocimene, para-cymene, phytol, pinene, pulegone, salvinorin, terpineol, terpinolene, or valencene.

Alpha-bisabolol, also known as levomenol, is a natural monocyclic sesquiterpene with a mild, floral, peppery odor.

It has also been used for hundreds of years in cosmetics because of its perceived skin healing properties. Bisabolol has been effective at blocking the effects of mutagens on genetic integrity in liver cells. Bisabolol has also exhibited strong effects on *Campylobacter* which are involved in severe food poisoning. Furthermore, bisabolol has been associated with pain relief and neuroprotection, with possible uses in Parkinson's and Alzheimer's.

Alpha-phellandrene has an aroma that is described as herbaceous, citrus, peppery, minty, and slightly green/woody. Strains containing large amounts of alpha-phellandrene can often be identified by their exceptionally minty taste. Alpha-phellandrene can be naturally sourced from corn parsley (*Ridolfia segetum*) and the elemi tree (*Canarium luzonicum*). Alpha-phellandrene is absorbed easily through the skin, a quality that has made it a valued substance in the perfume industry. Alpha-phellandrene has a long history in traditional Chinese medicine as a treatment for digestive disorders. More recent research has suggested that alpha-phellandrene possesses anti-depressive effects.

Alpha-pinene is an alkene and contains a highly reactive four membered ring perpendicular to the main ring, prone to skeletal rearrangements. Both the − and + enantiomers are seen in nature − alpha pinene is mostly seen in European pines, and + alpha pinene mostly in North American pines. The racemic mixture is seen in *eucalyptus* and citrus oils. Pinene is used in nature with the ozone to condense aerosols that could harm the environment.

Beta-caryophyllene is an important terpene found in *cannabis*. Beta-caryophyllene has been shown to act as a full agonist of the CB2-receptor, although it does not act on the CB1-receptor. It has also been shown to exert anti-inflammatory and analgesic effect. Beta-caryophyllene is a sesquiterpene, with a sweet, woody, spicy, clove-like smell. It is a unique terpene due to its large size and structure. Due to these properties, beta-caryophyllene is able to activate several receptors in the body, including CB2, which is usually activated most by CBD. Beta-caryophyllene has been shown to be an effective analgesic by regulating neuroinflammation and thermal hyperalgesia. Also as an antioxidant, beta-caryophyllene is effective as demonstrated by preventing lipid oxidation and scavenging other radicals. As an anti-inflammatory, beta-caryophyllene has been proven to mediate kidney inflammation and its side effects. Furthermore, beta-caryophyllene has been eluted to be a gastric-protective.

Bisabolol (also known as α-bisabolol or levomenol) is a fragrant chemical compound produced by the chamomile flower and other plants such as the candeia tree in Brazil. It is also produced by various *cannabis* strains. While it has long been widely used in the cosmetics industry, bisabolol has more recently become the subject of research for the medical benefits it displays in *cannabis*. Bisabolol's effects and benefits can include anti-inflammatory, anti-irritant, antioxidant, anti-microbial, and analgesic.

Borneol is a bicyclic monoterpene with a balsam, camphor, herbal, woody scent. Borneol is commonly used in Asian traditional medicine. Borneol has demonstrated more potent effects than the local anesthetic, lidocaine, and can also be eaten for its analgesic effects. Borneol has acted as an anticoagulant in stroke models, and alleviates the mechanisms of proinflammatory cytokines in general. The terpene has induced fungicidal activity against several species of fungi. In addition, borneol has elucidated to help drugs cross the blood brain barrier at a higher rate than without borneol.

Cadinenes are bicyclic sesquiterpenes. The term cadinene has sometimes also been used in a broad sense to refer to any sesquiterpene with the so-called cadalane (4-isopropyl-1,6-dimethyldecahydronaphthalene) carbon skeleton. Cadinene can be derived from that of the Cade juniper (*Juniperus oxycedrus* L.).

Camphene is a particularly pungent, herbaceous terpene that possesses a camphoraceous, cooling, woody aroma with notes of citrus and mint. In the 1900s Camphene was well known for its use as a fuel source for lamps and as a component of turpentine. Research suggests that camphene may be able to decrease nociceptive pain. Recent studies show that camphene may have a future in treating lung inflammation due to its promising ability to increase cell viability and improve mitochondrial membrane potential while decreasing lipid peroxidation.

Camphor has a strong, characteristic scent that is often familiar to those who have been acquainted with mothballs or Vicks® Vaporub™. Isolated camphor can be naturally sourced from the camphor laurel (*Cinnamomum camphora*), rosemary (*Rosmarinus oficinalis*), and the East African camphorwood (*Ocotea usambarensis*). Camphor has a historic past—the Chinese used it to embalm bodies and produce pigments used as ink. In medieval times bags of camphor in its powder or crystalline form were worn to defend from illness. In modern medicine, camphor is an active ingredient in various nasal decongestants and chest rubs. This is likely due to its anti-spasmodic and decongestant properties. Camphor has also been promoted as a natural insecticide.

Carene or delta 3-carene is terpene found in basil, bell peppers, rosemary, and *cannabis* that promotes the drying up of excess liquid and has anti-inflammatory effects. Side effects often associated with this terpene are dry mouth and red eyes. Carene has a pungent and pleasant earthy aroma that is piney in resemblance. Carene is a bicyclic monoterpene with a unique propanol ring; is has a sweet citrusy odor. Carene has been implicated in helping differentiate and stimulate calcium production in bone cells. The terpene is also effective as a toxin for mosquitos.

Caryophyllene oxide is an oxygenated terpinoid, usually a metabolic by product of caryophyllene. Its use as an antifungal is highly effective with certain species. In addition, caryophyllene oxide has also been indicated as an anticoagulant with platelets.

Citral exudes an aroma reminiscent of citrus (particularly lemon/lime). Isolated citral can be naturally sourced from lemon myrtle (Backhousia *citriodora*), lemongrass (Cymbopogon), lemon *verbena* (Aloysia citrodora), lemons, limes, and oranges. Citral's attractive scent has led it to be a favored ingredient in perfumes, soaps, and other cleaning products. Citral exhibits a gastro-protective effect (potentially useful for those suffering from gastrointestinal issues). It has been suggested that the inhalation of citral's fragrance may lead to normalized hormone levels, promoting homeostasis. Through this interaction with the body's neuroendocrine system, it is possible that citral may be used to treat those suffering from major depressive disorders.

Citronellol is a sweet, floral terpene with an aroma reminiscent of roses and citrus. Isolated citronellol can be naturally sourced from rose and geranium. Citronellol is used in perfumes, aromatherapy and has been approved by the FDA as safe for food use. A natural mosquito repellent and antimicrobial agent, citronellol is generally gentle when applied to the skin. Inhalation of citronellol may lead to deep sedation.

Eucalyptol, also known as 1,8 cineole, has a fresh, strong *eucalyptus*, camphoraceous, minty odor. It is a cyclic ether monoterpene. Eucalyptol has been popularly used on the skin, gums, or other topical areas. The terpene is toxic to several species of bacteria including *Staphylococcus aureus*. Further research has proven eucalyptol to be a potential treatment for Alzheimer's, as it lowered the inflammation caused by amyloid beta plaques. Eucalyptol is also an anti-inflammatory for sinuses and the digestive system. As an antioxidant, eucalyptol was effective at preventing lipid oxidation. In addition, eucalyptol has been effective in battling leukemia and colon cancer cells. Asthma remedies have also been used with eucalyptol.

Eugenol emits a strong, clove-like aroma. Isolated Eugenol can be naturally sourced from cloves (*Syzygium aromaticum*), wormwood (*Artemisia absinthium*), cinnamon (*Cinnamomum verum*), nutmeg (*Myristica fragrans*), and Japanese star anise (*Illicium anisatum*). Eugenol is a common additive in clove cigarettes. As it can have calming and anti-inflammation effects, it is popularly used in various perfumes and massage oils. Eugenol has antiseptic and anesthetic properties when applied topically. A combination of eugenol and tea tree oil is known to be effective in treating fungal infections.

Fenchol, or 1,3,3-trimethyl-2-norbomanol is a terpene and an isomer of borneol. The naturally occurring enantiopure (1R)-endo-(+)-fenchol is used extensively in perfumery. Fenchol is also, a scent from basil.

Gamma-terpinene has a sweetly herbaceous aroma augmented with notes of citrus. Isolated gamma-terpinene can be naturally sourced from tea tree (*Melaleuca alternifolia*) and *Lippia multiflora*. Gamma-terpinene is a major component of citrus essential oils. Its pleasant scent and taste has lead gamma-terpinene to be used widely as a flavor and fragrance additive in the cosmetic and food industries. Gamma-terpinene has exhibited antimicrobial properties and may be used to deflect a variety of human pathogens. Gamma-terpinene has also been noted as a promoter of antioxidant, anti-inflammatory, and antiproliferative activities.

Geraniol has a sweet, floral, fruity, rosy, waxy, citrus smell. The terpene has been known as a good mosquito repellent, but unfortunately attracts bees. Geraniol is toxic to bacteria and certain fungi. Further uses for the terpene include anti-inflammatory action. Also as a topical drug enhancer and anti-inflammatory, geraniol has proven useful.

Humulene is one of the main terpenes in hops, from which it gets its name. Humulene is also called alpha-caryophyllene. Like beta-caryophyllene, humulene is a cannabinoid and sesquiterpene, although it does not contain a cyclobutane ring. Humulene is a powerful anti-inflammatory and an anti-pain compound. It also has anti-cancer properties. Humulene is unique because, like THCV, it acts as an appetite suppressant, showing promise for weight loss treatments.

Limonene is a terpene found in certain strains of *cannabis* that conveys a pleasant citrus aroma. Limonene has been shown to help with inflammation, anxiety, acid reflux, allergies and depression. Limonene has been shown to be a potent antidepressant and anti-anxiety treatment comparable to some traditional medicines. Limonene has also been inferred to be an anti-inflammatory, lowering or preventing key stages in the reaction. Limonene was elucidated in being a potential treatment for breast, prostate and pancreatic cancer.

Linalool is a minor terpene found in certain strains of *cannabis* that is also produced in a variety of mints and herbs, including lavender. When combined with other major terpenes and cannabinoids, linalool may alleviate a number of conditions including pain, inflammation, depression, insomnia, anxiety and substance abuse. Linalool is a terpene alcohol with a citrusy, floral, sweet, bois de rose, woody, green, blueberry scent. Linalool is able to act on the opioidergic and cholinergic systems to relieve pain, a unique pathway for terpenes. Linalool also acts as an anticonvulsant, having similar effects to diazepam. Linalool has been used as a relaxant and as a treatment for anxiety for thousands of years. In scientific studies, linalool was proven to sedate mice and also mitigate anxiety.

Myrcene is the most commonly detected terpene in *cannabis*, and is a monoterpene that is an important precursor to many terpenes. Myrcene is also widely identified in plants, such as cloves, hops, lemon grass, and bay. It has been associated with having sedative, muscle relaxant and hypnotic properties and is commonly used for aromatic therapy of stress-relief. Myrcene is hypothesized to help compounds enter cells through enhancing membrane permeation. Myrcene has been shown to be an analgesic in mice and did not cause tolerance to the effect. Myrcene is also noted to have antioxidant effects with mutagenic compounds. Another benefit to myrcene is its ability to relax muscles and induce sleep.

Nerol is a strong, fresh terpene with a sweet rose aroma. Isolated nerol can be naturally sourced from neroli (*Citrus aurantium*), lemongrass (*Cymbopogon citratus*), and hops (*Humulus lupulus*). Nerol is used for its fragrance in perfumes and cosmetics and as a flavor agent in the food industry. Nerol may be used as a sedative, spasmolytic agent, and vasodilator. Nerol also possesses antiviral qualities.

Nerolidol is a sesquiterpene and that smells similar to fresh bark. There are two isomers present in nature, cis and trans. The terpene has been eluted to be a toxin against harmful protozoa like malaria and leishmaniasis. Furthermore, nerolidol is effect in delivering drugs through the skin.

Ocimene and beta-ocimene is a monoterpene with a fruity, floral, some say wet cloth smell. Ocimene has exhibited anti-inflammatory effects in white blood cell through a variety of pathways. Antifungal effects are also seen with the human specific *Candida* species. And very interestingly ocimene showed specificity and effectiveness against SARS virus.

Para-cymene is a constituent of a number of essential oils, most commonly the oil of cumin and thyme. Significant amounts are formed in sulfite pulping process from the wood terpenes.

Phytol is a mild floral terpene with a green, slightly balsamic aroma. Isolated phytol can be naturally sourced from barley (*Hordeum vulgare* L.) and green tea (*Camellia sinensis*). Phytol is a breakdown product in the decomposition of chlorophyll and acts as a precursor in the formation of vitamins E and K. Phytol plays an essential role in the human body by activating enzymes responsible for the production of insulin, and thereby helping to regulate blood glucose and cholesterol levels. Studies have shown that phytol may relieve insomnia, especially when used in conjunction with the terpene linalool. Phytol may also be used topically to reduce itchiness and treat wounds due to its anti-inflammatory and pain relieving qualities.

Pinene consists of two isomers, alpha and beta, depending on the position of the double bond within the molecule. Pinene is a terpene in *cannabis* that carries the aroma of pine. It is also present in orange peels, basil, pine needles and parsley. Pinene may help with asthma and anxiety, while reducing inflammation, enhancing relaxation and improving focus.

Pulegone emits a minty, faintly camphoraceous aroma. Isolated pulegone can be naturally sourced from pennyroyal (*Mentha pulegium*), catnip (*Nepeta cataria*), and peppermint (*Mentha piperita*). Pulegone is used by the candy and fragrance industries for its pleasant peppermint-like odor and flavor. Preservation and enhancement of memory is one of the effects of pulegone. This is due to pulegone's inhibition of the protein acetylcholinesterase. Thus, the memory is less affected by THC when it consumed with pulegone.

Terpineol has a citrusy, lime aroma with hints of lilac and apple blossom. Isolated terpineol can be naturally sourced from pine trees (*Pinus*), cajuput (*Melaleuca cajuputi*), and petitgrain (*Citrus aurantium*). Terpineol is most often used therapeutically to help manage pain and inflammation, and to reduce the frequency of seizures. Other medicinal values of terpineol include gastroprotection and promotion of antibacterial activities. Inhalation of terpineol may lead to a deep sedation.

Terpinolene is a terpene with a complex smoky, floral, herbal, or woody odor, commonly used in perfumes and soaps. It is naturally found in *cannabis* as well as other pleasantly fragrant plants including nutmeg, lilac, tea tree and apples. Terpinolene aids with sleep and may also be used to help fight bacterial or fungal infections. Terpinolene is a common terpene primarily isolated from trees. Terpinolene also goes by the name delta-terpinene. Terpinolene is not an analgesic or an anti-inflammatory, yet most cannabinoids and terpenoids are one of the two or both. Terpinolene was concluded to be effective against several species of bacteria. Terpinolene is able to increase total antioxidant capacity levels in white blood cells without changing the total oxidative stress level. Terpinolene is further effective in fighting glial cell cancer and leukemia.

Valencene is a bicyclic sesquiterpene with a sweet, fresh, citrusy, grapefruit, woody, orange odor. The terpene has been shown to be toxic and repel ticks and mosquitoes at lesser concentrations than DEET and without the toxicity to humans. Valencene has also been deduced to be and anti-inflammatory, lower the levels of inflammatory markers in macrophages.

As used herein, the term "primary terpene" refers to a terpene that is the most abundant terpene in a formulation either in absolute content as a % by dry weight, or in relative content as a % of the terpene in each formulation. For example, in a formulation comprising 5% limonene and 3% pinene, limonene would be the primary terpene.

As used herein, the term "secondary terpene" refers to a terpene that is the second most abundant terpene in a formulation either in absolute content as a % by dry weight, or in relative content as a % of the terpene in each formulation. For example, in a formulation comprising 5% limonene and 3% pinene, pinene would be the secondary terpene.

In an embodiment, the disclosure provides a formulation wherein the primary terpene is myrcene and the secondary terpene is linalool, and having a CBD:THC ratio of about 1:1 to about 1:5. In certain embodiments, the formulation comprises 5% myrcene, 3% linalool, and has a CBD:THC ratio of 1:1. In an embodiment, this formulation is essentially free of THC. In some embodiments, the disclosure relates to a method of treating a sleeping disorder by administering a pharmaceutically effective amount of the formulation.

*Cannabis* may help one fall asleep faster due its sleep-promoting effects. THC has well characterized sedative properties in rodents and humans. THC was also able to improve sleep in patients with obstructive sleep apnea and is being studied in restless legs syndrome.

THC (and CBD) may also improve sleep indirectly by relieving symptoms of other conditions that make sleeping difficult, including pain, anxiety, PTSD, and multiple sclerosis.

One study showed improved sleep quality in neuropathic pain patients after treatment with a mix of THC and CBD. CBD increased awake activity during sleep. For this reason, low CBD ratios are recommended near bedtime. However, CBD was also noted to have promise for excessive daytime sleepiness. CBN is a cannabinoid produced by degradation of THC through sunlight, heat and dry conditions. CBN is reported to have stronger sedative effects than THC itself.

Myrcene is a sedating terpene which is recognized by its musky, skunky smell. Its sedative and relaxing effects make it ideal for the treatment of insomnia and pain. Some contend that myrcene is the main *cannabis* terpene contributing to "couch-lock". Studies in rodents have shown that myrcene has several properties associated with sedatives, such as slowed motor activity, increased muscle relaxation, and increased sleeping time. Myrcene also exhibited anticonvulsant effects. Myrcene appears to work by enhancing activity of the inhibitory GABAA receptor. This mechanism is shared with benzodiazepines, which are sedative drugs used for anxiety and sleep. Some have proposed that myrcene works synergistically with THC to increase its sedative properties.

Studies in rodents have shown that myrcene has several properties associated with sedatives like for example prenobarbytal, which is evidenced by induction of P-450 (P-450 2B subfamily) enzyme (see PubMed ID (PMID): 8257941), slowed motor activity, increased muscle relaxation, and increased sleeping time. Myrcene also exhibited anti-convulsant effects. Recently, it was shown in rodent models that administration of J3-myrcene protects oxidative and histological damage in the heart tissue after global ischemia-reperfusion and may be useful safe alternative treatment for cardiac tissue after ischemic stroke (see PMID: 27487280). It can also exert fungistatic and fungicidal activities and serve as potent antioxidant (see PMID: 28680993; PMID: 21245202) Myrcene appears to work by enhancing activity of the inhibitory GABAA receptor.

This mechanism is shared with benzodiazepines, which are sedative drugs used for anxiety and sleep. Myrcene has a potential to be used as an analgesic, without developing tolerance to it. It appears to be a novel pain medication, without side effects of aspirin-like drugs, but more in human studies are needed (see PMID: 1753786). Some have proposed that myrcene works synergistically with THC to increase its sedative properties. Although, caution is warranted because high doses of myrcene might be anxiogenic (see PMID: 12587690).

Linalool may lessen the anxious emotions provoked by pure THC, thus making it helpful in the treatment of anxiety and other THC side effects. Linalool possesses anxiolytic and antidressant properties (see PMID: 26151006; PMID: 25771248). Studies in rodents have demonstrated the sedative effects of linalool, including decreased anxiety and reduced motor activity without a loss of coordination. Linalool also increased sleep and had anticonvulsant properties. Linalool may work in several ways. First, it is an antagonist of the NMDA receptor. This means that it can reduce activation of this receptor by glutamate, the main excitatory neurotransmitter of the brain. Other NMDA antagonists also have strong sedative properties. Second, it enhances GABAA activity, although it does this in a different way than myrcene since it does not bind the same receptor site. Based on the data in animal models, it might also possess antihypertensive properties, prevent development of cardiac hypertrophy, increase levels of the anti-inflammatory cytokine (IL-10), increase vasodilator responsiveness and reduce sensitivity to the sympathetic agonist (see PMID: 29454617). It has a beneficial potential for weight management and weight loss (see PMID: 29321988). Linalool may work in several ways. First, it is an antagonist of the NMDA receptor. This means that it can reduce activation of this receptor by glutamate, the main excitatory neurotransmitter of the brain. Other NMDA antagonists also have strong sedative properties. Second, it enhances $GABA_A$ activity, although it does this in a different way than myrcene since it does not bind the same receptor site.

In another embodiment, the disclosure provides a formulation wherein the primary terpene is pinene and the secondary terpene is terpineol, and having a CBD:THC ratio of about 20:1 to about 1:1. In certain embodiments, the formulation comprises 5% pinene, 3% terpineol, and has CBD:THC ratio of 4:1. In an embodiment, this formulation is essentially free of THC. In some embodiments, the disclosure relates to a method of improving concentration by administering a pharmaceutically effective amount of the formulation.

THC may cause temporary impairments in memory and concentration. For this reason, low THC ratios are recommended when one needs to concentrate. Interestingly, a low dose THC was able to boost brain levels of the neurotransmitter acetylcholine. Low THC doses could also stimulate neurogenesis, which was linked to cognitive improvements. CBD can reduce the impact of THC on memory. Although studies in humans are needed, CBD could reverse some hyperactivity patterns in rats. CBD can reduce the impact of THC on memory. More research on this topic is summarized in: PMID: 29432803; PMID: 29098186; PMID: 25799920; and PMID: 27811555.

Pinene is a reported to add a unique dimension to the personality of certain *cannabis* strains. Many strains with pinene as the dominant terpene are reported to promote alertness. Although the science behind the effects of pinene are not fully established, it is possible that pinene may improve memory through its antioxidant effects or boosting brain levels of acetylcholine. Acetylcholine is important for memory and cognition, but its release is decreased by THC. Through inhibition of acetylcholine metabolism, pinene and some other terpenes may improve cognitive impairment from THC. Pinene also had antidepressant effects in rodents, with mechanisms involving the serotonergic, adrenergic, and dopaminergic systems.

Terpineol can add a calming element that those with hyperactivity may find useful. Terpineol reduced locomotor activity in mice. Like some of the other *cannabis* terpenes, terpineol can enhance activity of the inhibitory GABAA receptor. Terpineol also possesses pain reducing properties, anti-nociceptive/reducing pain (see PMID: 29380385).

In yet another embodiment, the disclosure provides a formulation wherein the primary terpene is limonene and the secondary terpene is linalool, and having a CBD:THC ratio of about 20:1 to about 2:1. In certain embodiments, the formulation comprises 5% limonene and 3% linalool, and has a CBD:THC ratio of 1:1. In an embodiment, this formulation is essentially free of THC. In some embodiments, the disclosure relates to a method for treating stress or depression by administering a pharmaceutically effective amount of the formulation.

One of the important functions of the endocannabinoid system is adaptation to stress. Chronic stress is a risk factor for development and progression of depression and anxiety. THC can reduce anxiety, although it can also increase anxiety if the dose is too high. THC could be beneficial for certain disorders worsened by stress, such as migraines. In rodents, THC also showed antidepressant effects. CBD has shown anti-anxiety effects in humans, although studies are still ongoing. The mechanism appears to be both through the serotonin system and through boosting levels of endocannabinoids in the brain. CBD also showed antidepressant effects in rodents, although this has not been confirmed in humans. CBD could reduce certain side effects of THC, such as the psychotomimetic effects that occur in some people.

Limonene could contribute to an increase in attention span, mental focus and overall well-being. In rodents, limonene had anti-anxiety, anti-stress, and anti-depressant effects. Studies in rodents have demonstrated that linalool can decrease anxiety and reduce motor activity without a loss of coordination. In rat models with methamphetamine treatment, limonene reverses the increase in dopamine levels in the nucleus accumbens. These results suggest that limonene may inhibit stimulant-induced behavioral changes via regulating dopamine levels and 5-HT receptor function (see PMID: 24462212). S-limonene could also inhibit HPA reactivity under stress through the GABA(A) receptor (see PMID: 19763039), and exhibit anti-depressants properties (see PMID: 24661285).

During testing on the effects of limonene, participants experienced an increase in attention, mental focus, well-being and even libido. There are also undergoing trials for using limonene to treat depression and anxiety (see PMID: 22364736; PMID:24125633; www.sciencedirect.com/topics/pharmacology-toxicology-and-pharmaceutical-science/limonene; PMID: 23554130; PMC4670880; PMC3165946; www.oncologyreviews.org/article/view/oncol.2011.31; PMID: 25388013; and PMID: 24160248).

Linalool may increase sleep and possess anticonvulsant properties. Linalool may lessen the anxious emotions provoked by pure THC, thus making it helpful in the treatment of anxiety and other THC side effects. Linalool also possesses antidepressant properties, possibly through effects on the serotonin system. Linalool may work in several ways. First, it is an antagonist of the NMDA receptor. This means that it can reduce activation of this receptor by glutamate, the main excitatory neurotransmitter of the brain. Other NMDA antagonists also have strong sedative properties. Second, it enhances GABAA activity, although it does this in a different way than myrcene since it does not bind the same receptor site.

In an embodiment, the disclosure provides a formulation wherein the primary terpene is limonene and the secondary terpene is pinene, and having a CBD:THC ratio of about 1:1 to about 1:20. In certain embodiments, the formulation comprises 5% limonene and 3% pinene, and has a CBD:THC ratio of 1:2. In an embodiment, this formulation is essentially free of THC. In some embodiments, the disclosure relates to a method for treating fatigue by administering a pharmaceutically effective amount of the formulation.

CBD has been proposed as a treatment for excessive daytime sleepiness. *Cannabis* is also being tested in fibromyalgia, which includes chronic fatigue as a symptom. Although so far there is limited evidence of the efficacy of pure THC, some studies have shown improvements with medical *cannabis*.

Rodent studies indicate that limonene may reduce stress, anxiety, and depression, all of which can contribute to fatigue. Stress system activation was reduced by limonene through actions on the GABA system. Limonene may also have some regulation of the dopamine and serotonin systems, which are important for energy and motivation.

Pinene is a reported to add a unique dimension to the personality of certain *cannabis* strains. Many strains with pinene as the dominant terpene are reported to promote alertness.

High levels of pinene were associated with an excitatory effect in the brain. Pinene may also promote alertness through antioxidant effects or boosting brain levels of acetylcholine. However, controlled studies are needed in humans to confirm these effects.

In another embodiment, the disclosure provides a formulation wherein the primary terpene is linalool and the secondary terpene is borneol, and having a CBD:THC ratio of about 18:1 to about 4:1. In certain embodiments, the formulation comprises 5% linalool and 1% borneol, and has a CBD:THC ratio of 4:1. In some embodiments, the disclosure relates to a method for treating anxiety by administering a pharmaceutically effective amount of the formulation.

The relationship between THC and anxiety is complicated. Most people are aware that over-consuming THC is capable of causing anxiety and even panic. However, THC can reduce stress-induced anxiety when consumed at the appropriate dose. CBD is capable of reducing anxiety, both after a single dose and when consumed over time. CBD works in several different ways to counteract anxiety. CBD can have a rapid effect through activation of a type of serotonin receptor called the 5-HT1A receptor. CBD can also boost levels of naturally occurring endocannabinoids in the brain such as anandamide. Over time, anandamide can stimulate neurogenesis in certain parts of a subject's brain. This has been linked to improvements in anxiety and stress resilience. CBD is also able to reduce anxiety generated by THC.

Linalool has been used for centuries as a sleep aid. Linalool may lessen the anxious emotions provoked by pure THC, thus making it helpful in the treatment of anxiety and other THC side effects. Studies in rodents have demonstrated the sedative effects of linalool, including decreased anxiety and reduced motor activity without a loss of coordination. Linalool also increased sleep and had anticonvulsant properties. Linalool may work in several ways. First, it is an antagonist of the NMDA receptor. This means that it can reduce activation of this receptor by glutamate, the main excitatory neurotransmitter of the brain. Other NMDA antagonists also have strong sedative properties. Second, it enhances GABAA activity, although it does this in a different way than myrcene since it does not bind the same receptor site.

β-caryophyllene is the only *cannabis* terpene known to interact directly with the endocannabinoid system. It is a full agonist of the cannabinoid CB2 receptor. This means that β-caryophyllene is able to fully activate the CB2 receptor, whereas THC is generally only capable of partial activation. The CB2 receptor is present in many cell types throughout the body, but there are particularly high levels in immune cells. Activation does not result in an intoxicating effect, but it is an important regulator of inflammation and pain. CB2 activation resulted in improvement in several animal models of diseases, such as stroke, multiple sclerosis, Parkinson's disease, alcoholic liver disease, asthma, irritable bowel syndrome, and both neuropathic and inflammatory pain.

Borneol (also referred to as moxa) is a terpene in *cannabis* that can be used to relieve pain, reduce inflammation, lower anxiety, neuroprotectant, antioxidant, and treat heart disease. A study completed in 2013 (www.hindawi.com/j oumals/tswj/2013/808460/abs/) showed that this terpene produces a significant reduction of nociceptive pain while also displaying anti-inflammatory activity in mice. Unlike other medications used to treat pain and inflammation, borneol did not impair motor coordination. Another study from 2003 also confirmed that borneol can be used as a topical to numb pain and may be as effective as lidocaine (PMID: 12473382). In addition to reducing pain and inflammation, borneol can be used to manage anxiety.

In yet another embodiment, the disclosure provides a formulation wherein the primary terpene is beta-caryophyllene and the secondary terpene is humulene, and having a CBD:THC ratio of about 1:1 to about 1:10. In certain embodiments, the formulation comprises 5% beta-caryophyllene and 3% humulene, and has a CBD:THC ratio of 1:1. In an embodiment, this formulation is essentially free of THC. In some embodiments, the disclosure relates to a method for treating inflammation by administering a pharmaceutically effective amount of the formulation.

THC can activate both cannabinoid CB1 and CB2 receptors, which are expressed in many immune cells. Although CB2 is more commonly associated with an anti-inflammatory effect, CB1 also plays a role in activation of some immune cells. There are many studies demonstrating the anti-inflammatory properties of CBD. CBD general reduces activation of immune cells and has shown activity in many animal models of inflammatory and autoimmune conditions, including irritable bowel syndrome. The effect of CBD may involve activation of a type of intracellular receptors called PPARs, boosting endocannabinoid levels, or through other mechanisms. THC and CBD, both alone and in combination, have been tested in many studies of pain. This is a complex topic due to the number of different types of pain (inflammatory, neuropathic, migraine, etc.). Although there is still much to learn, these cannabinoids may be an effective way for some people to treat pain.

β-caryophyllene is the only *cannabis* terpene known to interact directly with the endocannabinoid system. It is a full agonist of the cannabinoid CB2 receptor. This means that β-caryophyllene is able to fully activate the CB2 receptor, whereas THC is generally only capable of partial activation. The CB2 receptor is present in many cell types throughout the body, but there are particularly high levels in immune cells. Activation does not result in an intoxicating effect, but it is an important regulator of inflammation and pain. CB2 activation resulted in improvement in several animal models of diseases, such as stroke, multiple sclerosis, Parkinson's disease, alcoholic liver disease, asthma, irritable bowel syndrome, and both neuropathic and inflammatory pain. For example, CB2 activation has improved several animal models of diseases (see bmcneurol.biomedcentral.com/articles/10.1186/1471-2377-6-12, such as stroke, multiple sclerosis, Parkinson's disease, alcoholic liver disease, asthma, irritable bowel syndrome, Inflamation onlinelibrary.wiley.com/doi/10.1111/j.1471-4159.2005.03380.x/full and both neuropathic and inflammatory pain; onlinelibrary.wiley.com/doi/10.1038/sj.bjp.0707505/full).

Humulene has been used in Chinese medicine for generations. Humulene possesses both anti-inflammatory and pain reducing properties, as well as immune boosting properties (see PMID: 17559833; herb.co/marijuana/news/humulene; PMID: 18053325; PMID: 12802719; and PMID: 19921589). The anti-cancer properties of humulene were first highlighted in a 2003 study (see PMID: 12802719), which suggests it may be a result of humulene's ability to produce Reactive Oxygen Species (ROS). ROS have various roles in cancer, contributing to the death of cancer cells through apoptosis at some levels; although at other levels ROS can actually increase the growth rate of tumors. Both ROS maximizing and ROS minimizing approaches have been developed and are commonly used, though ROS maximizing strategies seem to be more common. A demonstration of the entourage effect can be seen in a 2007 study (see PMID: 18053325), which showed that β-caryophyllene potentiates the anti-cancer effects of humulene.

In an embodiment, the disclosure provides a formulation wherein the primary terpene is beta-caryophyllene and the secondary terpene is myrcene, and having a CBD:THC ratio of about 1:1 to about 1:6. In certain embodiments, the formulation comprises 5% beta-caryophyllene and 5% myrcene, and has a CBD:THC ratio of 1:2. In an embodiment, this formulation is essentially free of THC. In some embodiments, the disclosure relates to a method for improving wellness by administering a pharmaceutically effective amount of the formulation.

β-caryophyllene is the only *cannabis* terpene known to interact directly with the endocannabinoid system. It is a full agonist of the cannabinoid CB2 receptor. This means that β-caryophyllene is able to fully activate the CB2 receptor, whereas THC is generally only capable of partial activation. The CB2 receptor is present in many cell types throughout the body, but there are particularly high levels in immune cells. Activation does not result in an intoxicating effect, but it is an important regulator of inflammation and pain. CB2 activation resulted in improvement in several animal models of diseases, such as stroke, multiple sclerosis, Parkinson's disease, alcoholic liver disease, asthma, irritable bowel syndrome, and both neuropathic and inflammatory pain.

Myrcene is a sedating terpene which is recognized by its musky, skunky smell. Its sedative and relaxing effects make it ideal for the treatment of insomnia and pain. Some claim that myrcene is the main *cannabis* terpene contributing to "couch-lock". Studies in rodents have shown that myrcene has several properties associated with sedatives, such as slowed motor activity, increased muscle relaxation, and increased sleeping time. Myrcene also exhibited anti-convulsant effects. Myrcene appears to work by enhancing activity of the inhibitory GABAA receptor. This mechanism is shared with benzodiazepines, which are sedative drugs used for anxiety and sleep. Some have proposed that myrcene works synergistically with THC to increase its sedative properties.

In an embodiment, the disclosure provides a formulation comprising less than about 0.03% THC, and having a CBD:THC ratio of about 1:0.2 to about 1:0. In an embodiment, this formulation is essentially free of THC.

Cannabidiol, (CBD) is the major non-psychoactive component of *Cannabis sativa*. CBD activates 5-HT1A serotonin receptor, which helps with anxiety, addiction, appetite, sleep, nausea, vomiting. It also binds to TRPV1 receptors, which moderates perception of pain, inflammation, body temperature as well as blocks G protein receptor GPR55, which may decrease bone reabsorption and the spread of cancer cells. CBD activates peroxisome proliferator activated receptors (PPARs), which has been shown to produce anti-cancer effect and help with Alzheimer's. CBD benefits include acting in some experimental models as an anti-inflammatory, anticonvulsant, antioxidant, antiemetic, anxiolytic and antipsychotic agent, and is therefore a potential medicine for the treatment of neuro-inflammation, epilepsy, oxidative injury, vomiting and nausea, anxiety and schizophrenia.

In an embodiment, the disclosure provides a powder-based formulation that is encapsulated for oral administration, and having a CBD:THC ratio of about 1:1 to about 1:3.

In certain embodiments, the formulation comprises branched-chain amino acids (BCAA; L-leucine, L-isoleucine, L-valine), L-glutamine, piperine (for example, BioPerine®), Magnesium stearate, MCC, or silicon dioxide. In an embodiment, the formulation has a CBD:THC ratio of about 1:2. In an embodiment, this formulation is essentially free of THC. In some embodiments, the disclosure relates to a method for improving recovery (for example, following a workout or exercise) by administering a pharmaceutically effective amount of the formulation.

Piperine may help with nutrient absorption through its ability to increase the level of absorption of nutrients (referred to as "bioenhancement"), and improve metabolism as well as immune function. Piperine may also help improve dopamine and serotonin levels, which can improve memory and mental skills Branched-chain amino acids (BCAA) are amino acids having an aliphatic side-chain with a branch, and include leucine, isoleucine, and valine. BCAAs are among the essential amino acids for humans, accounting for 35% of the essential amino acids in muscle proteins and 40% of the preformed amino acids required by mammals. BCAAs fill several metabolic and physiologic roles. Metabolically, BCAAs promote protein synthesis and turnover, signaling pathways, and metabolism of glucose. Oxidation of BCAAs may increase fatty acid oxidation and play a role in obesity. Physiologically, BCAAs take on roles in the immune system and in brain function. BCAAs are broken down effectively by dehydrogenase and decarboxylase enzymes expressed by immune cells, and are required for lymphocyte growth and proliferation and cytotoxic T lymphocyte activity. Lastly, BCAAs share the same transport protein into the brain with aromatic amino acids (Trp, Tyr, and Phe). Once in the brain BCAAs may have a role in protein synthesis, synthesis of neurotransmitters, and production of energy.

In some embodiments of the formulations as disclosed herein, the formulations can comprise less than about 25%, about 20%, about 15%, about 10%, about 5%, about 4%, about 3%, or about 2% or less of any one terpene. In certain embodiments, the formulations as disclosed herein can comprise 0%, 0.01%, 0.02%, 0.04%, 0.06%, 0.08%, 0.10%, 0.12%, 0.14%, 0.16%, 0.18%, 0.20%, 0.22%, 0.24%, 0.26%, 0.28%, 0.30%, 0.32%, 0.34%, 0.36%, 0.38%, 0.40%, 0.42%, 0.44%, 0.46%, 0.48%, 0.50%, 0.52%, 0.54%, 0.56%, 0.58%, 0.60%, 0.62%, 0.64%, 0.66%, 0.68%, 0.70%, 0.72%, 0.74%, 0.76%, 0.78%, 0.80%, 0.82%, 0.84%, 0.86%, 0.88%, 0.90%, 0.92%, 0.94%, 0.96%, 0.98%, 1.0%, 1.02%, 1.04%, 1.06%, 1.08%, 1.10%, 1.12%, 1.14%, 1.16%, 1.18%, 1.20%, 1.22%, 1.24%, 1.26%, 1.28%, 1.30%, 1.32%, 1.34%, 1.36%, 1.38%, 1.40%, 1.42%, 1.44%, 1.46%, 1.48%, 1.5%, 1.6%, 1.7% 1.8%, 1.9%, 2.0%, 2.2%, 2.4%, 2.6%, 2.8%, 3%, 3.2%, 3.4%, 3.6%, 3.8%, 4.0%, 4.2%, 4.3%, 4.4%, 4.6%, 4.8%, 5.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6%, 9.8%, 10.0%, 11.0%, 12.0%, 13.0%, 14.0%, 15.0%, 16.0%, 17.0%, 18.0%, 19.0%, 20.0%, 25.0%, or greater based on dry weight. In some embodiments the absolute content of any one terpene can be between about 0.01% and about 25.0%.

In some embodiments of the formulations as disclosed herein, the formulations can comprise from about 0.1 mg/mL to about 100 mg/mL of the CBD. In certain embodiments, the formulations as described herein comprise 0.01 mg/mL, 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg/mL, 4.8 mg/mL, 4.9 mg/mL, 5.0 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL or more of CBD. In some embodiments, the formulations as described herein comprise 0.01 g, 0.02 g, 0.03 g, 0.04 g, 0.05 g, 0.06 g, 0.07 g, 0.08 g, 0.09 g, 0.1 g, 0.2 g, 0.025 g, 0.3 g, 0.4 g, 0.5 g, 0.6 g, 0.7 g, 0.8 g, 0.9 g, 1.0 g, 1.1 g, 1.2 g, 1.3 g, 1.4 g, 1.5 g, 1.6 g, 1.7 g, 1.8 g, 1.9 g, 2.0 g, 2.1 g, 2.2 g, 2.3 g, 2.4 g, 2.5 g, 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, 5.0 g, 10 g, 15 g, 20 g, 25 g, 30 g, 35 g, 40 g, 45 g, 50 g, 55 g, 60 g, 65 g, 70 g, 75 g, 80 g, 85 g, 90 g, 95 g, 100 g, or more of CBD.

In some embodiments of the formulations as disclosed herein, the formulations can comprise from about 0.1 to about 100 mg/mL of the THC; however in certain embodiments the formulation may not contain THC, or are essentially free of THC. In certain embodiments, the formulations as described herein comprise 0.00 mg/mL, 0.01 mg/mL, 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg/mL, 4.8 mg/mL, 4.9 mg/mL, 5.0 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL or more of THC. In some embodiments, the formulations as described herein comprise, 0.00 g, 0.01 g, 0.02 g, 0.025 g, 0.03 g, 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1.0 g, 1.1 g, 1.2 g, 1.3 g, 1.4 g, 1.5 g, 1.6 g, 1.7 g, 1.8 g, 1.9 g, 2.0 g, 2.1 g, 2.2 g, 2.3 g, 2.4 g, 2.5 g, 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, 5.0 g, 10 g, 15 g, 20 g, 25 g, 30 g, 35 g, 40 g, 45 g, 50 g, 55 g, 60 g, 65 g, 70 g, 75 g, 80 g, 85 g, 90 g, 95 g, 100 g, or more of THC.

A formulation is said to be "essentially free" of a particular component (i.e., THC, CBD, or a terpene), if that particular component is absent from the formulation or if the particular component is present in the formulation, but in an amount which is insufficient to promote any substantial effect in a subject, or is present at a concentration below a detectable limit. Additionally, it will be recognized that a formulation which is essentially free of a particular component may nonetheless contain trace amounts of the particular component in the formulation. For example, a formulation may contain no intentionally added THC and/or may contain no THC within conventional detection limits (thus, the term "essentially free of THC" encompasses the term "lacking THC").

In certain embodiments of the formulations as disclosed herein, the formulations can comprise less than about 5%, about 4%, about 3%, or about 2%, or about 1% or less of any one or more of: black pepper, branched-chain amino acids (BCAA), cayenne, cedarwood, chamomile, coconut oil, geranium, ginger, ginger oil, glutamine, guava, juniper berry, lavender, lemon, lemon oil, lemongrass, lime, lime oil, orange, orange oil, mango, marjoram, menthol, mint, mint oil, peppermint, peppermint oil, piperine, geranium, rosemary, sandalwood, or tangerine. In certain embodiments, the formulations as disclosed herein can comprise about 0.01%, 0.02%, 0.04%, 0.06%, 0.08%, 0.10%, 0.12%, 0.14%, 0.16%, 0.18%, 0.20%, 0.25%, 0.30%, 0.40%, 0.50%, 0.60%, 0.70%, 0.80%, 0.90%, 1.0%, 1.1%, 1.2%, 1.3%, 1.4%, 1.5%, 1.6%, 1.7%, 1.8%, 2.0%, 2.2%, 2.4%, 2.6%, 2.8%, 3%, 3.2%, 3.4%, 3.6%, 3.8%, 4.0%, 4.2%, 4.3%, 4.4%, 4.6%, 4.8%, 5.0% or greater based on dry weight.

In some embodiments, the formulations are formulated for buccal, dermal, intranasal, intravenous, nasal, ophthalmic, oral, sublingual, topical, or transdermal administration. As different medical conditions can warrant different routes of administration, various forms for a particular formulation may exist. Methods for administration of the formulations described herein include, but are not limited to, inhalation (for example, dry powder inhalers, vaporizers, nebulizers, metered dose inhalers), smoking (e.g., dried buds), drinking, eating extracts or food products infused with concentrates or extracts, and taking capsules.

Exemplary forms can include, but are not limited to, adhesive topical patch, aerosol, balm, capsule, chewing gum, cream, drops, elixir, emulsion, film, gas, gel granule, hydrogel, liniment, liquid, lollipop, lotion, lozenge, ointment, paste, pill, powder, skin patch, spray, strip, syrup, tablet, or tincture (a solvent extract of plant or animal material, or of a low volatility substance). For example, a composition formulated for oral administration can comprise a liquid gel capsule, a soft gel capsule, a tablet, a chewable tablet, a chewable wafer, an extended release formulation, a "gummy" candy (chewable lozenge; e.g. pectin or gelatin base), a lozenge, a pastille (e.g. polyol base), chewing gum, an effervescing tablet, or a liquid formulation. Gummies, lozenges, tablets, and capsules may, for example, be generated with sugar or as sugar free formulations.

In some embodiments, the formulations further comprise one or more of: binders, natural flavoring agents, artificial flavoring agents, disintegrants, emulsifiers, glidants (flow aids), granulating agents, natural colorants, artificial colorants, lubricants, preservatives, or sweetening agents. The formulations may include varied and numerous inactive ingredients known within the art to improve the formulation, delivery, preservation, appearance, palatability, and administration of the active ingredients.

In some embodiments, formulations are low in sugar (<40% sugar, less than about 30% or less than about 20% sugar), or are sugar-free. Sugar substitutes can include, but are not limited to, aspartame, sucralose, saccharin, stevia, monk fruit sweetener, erythritol, sorbitol, xylitol, mannitol, maltitol, and hydrogenated glucose or maltose syrups or maltodextrins, or combinations thereof.

Non-limiting examples of binders can include: acacia, tragacanth, gelatin, starch, cellulose based materials such as methyl cellulose and sodium carboxy-methyl cellulose, alginic acids and salts thereof, magnesium, aluminum silicate, polyethylene glycol, guar gum, polysaccharide acids, bentonites, sugars, invert sugars and the like.

Non-limiting examples coloring agents can include: known FD&C dyes and natural coloring agents such as grape skin extract, beet red powder, beta-carotene, annatto, carmine, turmeric, or paprika. The amount of coloring used may range from about 0.05 to about 5% by weight of the total composition.

Non-limiting examples of optional flavoring agents can include: synthetic flavors oils and flavoring aromatics, natural oils, plant extracts. Examples include almond oil, anise oil, avocado oil, bay oil, canola (rapeseed) oil, cedar leaf oil, cinnamon oil, coconut oil, clove oil, *eucalyptus*, flaxseed oil, grape seed oil, macadamia oil, nutmeg oil, olive oil, oil of wintergreen, peanut oil, peppermint oil, pine kernel oil, pomegranate seed oil, pumpkin seed oil, safflower oil, sesame oil, sage oil, soya bean oil, sunflower oil, thyme oil, omega 3 fatty acids (for example, ALA (alpha-linolenic acid), EPA (eicosapentaenoic acid) and DHA (docosahexaenoic acid)), omega 9 fatty acids, and combinations thereof. Examples of flavoring agents can also include, but are not limited to, almond, apple, banana, berry, bubblegum, caramel, citrus, cherry, chocolate, coconut, grape, green tea, honey, lemon, licorice, lime, mango, maple, mint, orange, peach, pineapple, raisin, strawberry, vanilla, watermelon, and combinations thereof. Flavoring agents may be present in an amount ranging from about 0.05 to about 5% by weight of the total composition.

Non-limiting examples of emulsifiers can include: lecithin, polysorbates, or sorbitan monooleates, and combinations thereof.

In certain embodiments, the formulations may further comprise an ingredient useful for increasing the storage stability of the formulations. In some embodiments this is an antioxidant. Suitable antioxidants can include molecules that inhibit the oxidation of other molecules. Non-limiting examples of antioxidants can include, but are not limited to, vitamin A, vitamin C, vitamin E, alpha-carotene, astaxanthin, beta-carotene, canthaxanthin, lutein, lycopene, zeaxanthin, flavonoids (such as apigenin, myricetin, eriodictyol, theaflavin, genistein, resveratrol, malvidin), cinnamic acid, chicoric acid, chlorogenic acid, rosmarinic acid, curcumin, xanthones, eugenol, citric acid, oxalic acid, and lipoic acid.

In an aspect, the disclosure relates to methods for treating a subject comprising: (a) determining the subject's DNA genotype; (b) matching the subject with a formulation as disclosed herein based on the subject's DNA genotype; and (c) administering a pharmaceutically effective amount of the formulation to the subject. In some embodiments of the method of treating a subject, the subject's DNA genotype is assessed to identify one or more single nucleotide polymorphisms (SNPs), and based on the SNP, a pharmaceutically effective amount of any of the formulations as disclosed herein is administered to the subject. A number of exemplary SNPs, with formulations, are discussed in Table 10.

In some embodiments, the formulations disclosed herein can be used to treat one or more of the following: acquired hypothyroidism, acute gastritis, agoraphobia, aids related illness, alcohol abuse, alcoholism, alopecia areata, Alzheimer's disease, amphetamine dependency, amyloidosis, amyotrophic lateral sclerosis (ALS), angina pectoris, ankylosis, ankylosing spondylitis, anorexia, anorexia nervosa, anxiety disorders, any chronic medical symptom that limits major life activities, any chronic medical symptom that limits major life activities, arteriosclerotic heart disease, arthritis, arthritis (rheumatoid), arthropathy, gout, asthma, attention deficit hyperactivity disorder (ADD/ADHD), autism, autoimmune disease, back pain, back sprain, Bell's palsy, bipolar disorder, brain tumor, malignant, bruxism, bulimia, cachexia, cancer, carpal tunnel syndrome, cerebral palsy, cervical disk disease, cervicobrachial syndrome, chemotherapy chronic fatigue syndrome, chronic pain, chronic renal failure, cocaine dependence, colitis, conjunctivitis, constipation, Crohn's disease, cystic fibrosis, damage to spinal cord nervous tissue, Darier's disease, degenerative arthritis, degenerative arthropathy, delirium tremens, dermatomyositis, diabetes, diabetic neuropathy, diabetic peripheral vascular disease, diarrhea, diverticulitis, dysthymic disorder, eczema, emphysema, emphysema, endometriosis, epidermolysis bullosa, epididymitis, epilepsy, Felty's syndrome, fibromyalgia, Friedreich's ataxia, gastritis, genital herpes, glaucoma, glioblastoma multiforme, Graves disease, cluster headaches, migraine headaches, tension headaches, hemophilia a, Henoch-Schonlein purpura, hepatitis C, hereditary spinal ataxia, HIV/AIDS, hospice patients, Huntington's disease, hypertension, hypertension, hyperventilation, hypoglycemia, impotence, inflammatory autoimmune-mediated arthritis, inflammatory bowel disease (IBD), insomnia, intermittent explosive disorder (IED), intractable pain, intractable vomiting, lipomatosis, Lou Gehrig's disease, lyme disease, lymphoma, major depression, malignant melanoma, mania, melorheostosis, Meniere's disease, motion sickness, mucopolysaccharidosis (MPS), multiple sclerosis (MS), muscle spasms, muscular dystrophy, myeloid leukemia, nail-patella syndrome, nightmares, obesity, obsessive compulsive disorder, opiate dependence, osteoarthritis, panic disorder, Parkinson's disease, peripheral neuropathy, peritoneal pain, persistent insomnia, *porphyria*, post-polio syndrome (PPS), post-traumatic arthritis, post-traumatic stress disorder (PTSD), premenstrual syndrome (PMS), prostatitis, psoriasis, pulmonary fibrosis, quadriplegia, radiation therapy, Raynaud's disease, Reiter's syndrome, restless legs syndrome (RLS), rheumatoid arthritis, rosacea, schizoaffective disorder, schizophrenia, scoliosis, sedative dependence, seizures, senile dementia, severe nausea, shingles (herpes zoster), sinusitis, skeletal muscular spasticity, sleep apnea, sleep disorders, spasticity, spinal stenosis, Sturge-Weber syndrome (SWS), stuttering, tardive dyskinesia (TD), temporomandibular joint disorder (TMJ), tenosynovitis, terminal illness, thyroiditis, tic douloureux, Tietze's syndrome, tinnitus, tobacco dependence, Tourette's syndrome, trichotillomania, viral hepatitis, wasting syndrome, whiplash, Wittmaack-Ekbom's syndrome, writers' cramp, nausea, vomiting, unintentional weight loss, insomnia, and lack of appetite, spasticity, painful conditions, especially neurogenic pain, movement disorders, asthma, glaucoma, adrenal disease, migraines, fibromyalgia, and related conditions, spinal cord injuries. The formulations disclosed herein can exhibit antispasmodic and muscle-relaxant properties as well as stimulates appetite, and may be useful in treating alcohol abuse, amyotrophic lateral sclerosis, collagen-induced arthritis, asthma, atherosclerosis, bipolar disorder, colorectal cancer, HIV-associated sensory neuropathy, depression, dystonia, epilepsy, digestive diseases, gliomas, hepatitis C, Huntington's disease, leukemia, skin tumors, methicillin-resistant *Staphylococcus aureus* (MRSA), Parkinson's disease, pruritus, posttraumatic stress disorder (PTSD), psoriasis, sickle-cell disease, sleep apnea, and anorexia nervosa. In other embodiments, the formulations as disclosed herein can be used for recreational purposes.

Anxiety is a common disorder experienced by many individuals. While the study behind the causes and effects of anxiety are ever changing, there have been several SNPs discovered that relate to the interaction of anxiety and cannabinoids. For example, the SNP rs1049353 for the CNR1 gene is associated with activation of specific brain areas (the insula and amygdala). The effect of this related to how one gauges visual, emotional, and social cues. Examples include facial expressions that change from anger to sadness or fear; happiness to sadness or fear; and neutral. Another example is the SNP rs324420 for the FAAH gene, which is associated with how an individual's endocannabinoid system (ECS) is related to specific neural mechanisms which may impact complex behavioral processes related to risk for addiction, dependence, and obesity. Yet another example is the SNP 5-HTTLPR for the SLC6A4 gene, which is associated with the development of anxiety for youth users of *cannabis*. By analyzing these SNPs, a subject at risk for anxiety or suffering from anxiety may be effectively treated with the formulations as disclosed herein.

Bipolar disorder, or manic depression, is a serious brain illness that causes unusual shifts in mood, energy, activity, and the ability to carry out daily activities. Individuals suffering from bipolar disorder experience periods of intense emotion, changes in sleep, and unusual behavior, known as episodes. Episodes can be categorized as either manic (more energetic and "up" than normal) or depressive (more low energy and "down" than normal). While research surrounding bipolar disorder is ever changing, researchers have identified a SNP associated with the risk for developing bipolar disorder. For example, the SNP rs41311993 for the CNR2 gene is associated with the risk for developing bipolar disorder. By analyzing these SNPs, a subject at risk for developing bipolar disorder or suffering from bipolar disorder may be effectively treated with the formulations as disclosed herein.

Cognitive function may, for example, relate to a user's ability of their brain to process information and knowledge. While this is a general trait, researchers have identified SNPs that indicate how *cannabis* may affect a user's cognitive function. In one example, the SNP rs1049353 for the CNR1 gene is associated with lower performance of executive function and sustained attention. Thus, depending on their endocannabinoid genotype, some users may experience an elevated risk of not being able to sustain attention when using *cannabis*. In another example, the SNP rs4680 for the COMT gene is associated with risk of structural brain changes following *cannabis* use. Users that have an at-risk genotype for this SNP (e.g., homozygous alleles, such as (A/A)), may want to consult with a specialist in cognitive function before using *cannabis*. In yet another example, the SNP rs12199654 for the MAPK14 gene is associated with a risk of decreased white matter brain volume from *cannabis* use, which may result in impairing a user's cognitive function. In another example, the SNP rs7834206 for the NRG1 gene is associated with auditory reception when using *cannabis*. Users with heterozygous alleles (C/A) may be more likely to have auditory discrepancies after using *cannabis* when compared to users with other genotypes. In yet another example, the SNP 5-HTTLPR for the SLC6A4 gene is associated with a user's focus, visual interpretation of their environment, and decision making. Users with homozygous alleles (L'/L') might not experience a decrease in brain performance when using *cannabis*. By analyzing these SNPs, the cognitive function of a subject may be effectively treated and/or improved with the formulations as disclosed herein.

Depression may, for example, relate to how a user feels, thinks, and acts. Specifically, depression is a long-term mental degradation that can affect the way a user functions in daily life. Depression can further be characterized by feeling tearful, irritable, and having diminished interest or pleasure in activities every day; significant weight loss/decrease or increase in appetite; inability to get to sleep or difficulty staying asleep or sleeping too much; problems with sitting or a slowing of one's movements; talking very quietly with slowed speech; fatigue; tiredness; feelings of worthlessness; diminished ability to think or concentrate; recurrent thoughts of death (not just fear of dying); recurrent suicidal ideas without a specific plan; or a suicide attempt or creating a specific plan for committing suicide. Due to the severity of depression symptoms, it is beneficial to have an understanding of how *cannabis* may affect users that have a particular genotype. For example, the SNP rs1049353 for the CNR1 gene is associated with depression—specifically, how a user reacts to certain antidepressants such as citalopram. Users that have heterozygous alleles (C/T) may have a decrease likelihood of responding to antidepressants. In another example, the SNP rs2023239 for the CNR1 gene is associated with depression generally. Users that have homozygous alleles (T/T) may experience a higher likelihood of exacerbating pre-existing symptoms of depression when using *cannabis*. In yet another example, the SNP rs806377 for the CNR1 gene is associated with how a user responds to positive emotional stimuli. Users with homozygous alleles (T/T) may experience a higher amount of positive emotions after a positive event than people with heterozygous alleles. In yet another example, the SNP rs324420 for the FAAH gene is associated with white matter integrity in the brain and increased reports of depression and apathy in *cannabis* users. Users with homozygous alleles (CC) may experience decreased white matter in the brain and weakened brain structure when *cannabis* is used at a young age. By analyzing these SNPs, a subject at risk for developing depression or suffering from depression may be effectively treated with the formulations as disclosed herein.

Impulsive behavior may, for example, relate to making decisions without thinking of the results and/or consequences beforehand. Impulsive behavior has many causes, which can include mental disorders such as hyperactivity disorder or personality disorders, such as borderline personality disorder. *Cannabis* usage may also cause impulsivity for certain users. For example, the SNP rs1049353 for the CNR1 gene is associated with adolescent psychosocial adversity, which is how one responds and/or adapts to family or relationship problems, health problems, school and other structural worries, and how they relate to impulsive behavior. Users with a genotype containing heterozygous alleles (C/T) may have an elevated risk of impulsive behavior when using *cannabis*. In another example, the SNP rs806379 for the CNR1 gene is also associated with adolescent psychosocial adversity. Users with homozygous alleles (A/A) that experienced early psychosocial adversity may have a higher risk of impulsive behavior. In yet another example, the SNP rs1611115 for the DBH gene is associated with impulsivity after *cannabis* consumption. Users with homozygous alleles (C/C) might not have increased impulsivity after *cannabis* use, while users with heterozygous alleles may have increased impulsivity after *cannabis* use. In yet another example, the SNP rs221533 for the NRG1 gene is associated with lower inhibition and significantly riskier decision making. Users with heterozygous alleles (T/C) may have a lower risk of having behaviors associated with risky decision making when using *cannabis*. In yet another example, the SNP rs28363170 for the SLC6A3 gene is also associated with impulsivity when using *cannabis*. Users with homozygous alleles (10R/10R) may have a lower risk of impulsivity after consuming *cannabis* compared to users with heterozygous alleles. By analyzing these SNPs, a subject at risk for developing impulsive behavior or suffering from impulsive behavior may be effectively treated with the formulations as disclosed herein.

Memory impairment may, for example, relate to a person's ability to store information in their brain. For example, the SNP rs1049353 for the CNR1 gene is associated with varying brain awareness states, which is related to working memory ability and other cognitive functions. Users with heterozygous alleles (C/T) may have a normal state of awareness when compared to users with a different genotype. In another example, the SNP rs1406977 for the CNR1 gene is associated with performance on working memory tasks when using *cannabis*. Users with homozygous alleles (T/T) may be less likely to experience working memory impairments after use of THC. By analyzing these SNPs, a subject at risk for developing memory impairment or suffering from memory impairment may be effectively treated with the formulations as disclosed herein.

Metabolic function may, for example, relate to how a user's cells breaks down materials from food to energy. Metabolic function may vary in users that are consuming *cannabis*. For example, the SNP rs1045642 for the ABCB1 gene is associated with THC levels and THC metabolites in *cannabis* users. Users with homozygous alleles (T/T) may have two-fold lower blood THC levels after consuming THC relative to people with a different genotype. In another example, the SNP rs1057910 for the CYP2C9 gene is associated with how oral THC is processed or metabolized in the body. Users with homozygous alleles (A/A) are typically no more sensitive to oral THC. By analyzing these SNPs, the metabolic function of a subject may be effectively treated and/or improved with the formulations as disclosed herein.

Migraines may, for example, relate to severe headaches that occur on one side of the head. Migraines can cause extreme discomfort and symptoms such as nausea and oversensitivity to lights and sounds. Research indicates that *cannabis* usage may have an effect on migraines in certain individuals. For example, the SNP rs806366 for the CNR1 gene is associated with a user's susceptibility to migraines. Users with homozygous alleles (T/T) may be more likely to develop migraines after stressful events. This is beneficial information because a medical provider can prescribe an appropriate dose if the provider is aware that the user is more likely to develop migraines. By analyzing these SNPs, a subject at risk for developing migraines or suffering from migraines may be effectively treated with the formulations as disclosed herein.

Motor control may, for example, relate to the process of creating and sending purposeful, voluntary movements throughout the body. Research indicates that the consumption of *cannabis* may have profound effects on a user's motor control. For example, the SNP rs1130233 for the AKT1 gene is associated with the degree of impairment in a user's psychomotor control and/or motor coordination after consumption of THC. Users with heterozygous alleles (C/T) may develop impaired motor coordination and slowed down thinking after consuming THC. By analyzing these SNPs, motor control in subject may be effectively treated and/or improved with the formulations as disclosed herein.

Opioids are, for example, a class of drugs created from the opium poppy plant. The plants are harvested and used in various types of medications because they contain a chemical that relaxes the body, and helps to relieve pain. Examples of opioids include Hydrocodone, Oxycodone, Oxymorphone, Morphine, Fentanyl, and Codeine. Research indicates that particular genetic markers may affect how a user reacts to opioids. For example, the SNP rs324420 for the FAAH gene is associated with having adverse opioid effects when combined with how a user's endocannabinoid system modulates, by way of such cannabinoids such as anandamide. Users with homozygous alleles (C/C) may have a lower risk of experienced side effects from opioids relative to people with a different genotype. By analyzing these SNPs, a subject at risk for developing opioid dependence or suffering from opioid dependence may be effectively treated with the formulations as disclosed herein.

Pain may, for example, relate to the unpleasant and corresponding emotional reaction in response to injury or tissue damage. Pain is a signal sent through the spinal cord, to a user's brain, alerting her that something is wrong in her body. Pain can be difficult to diagnose as it can manifest itself in different ways for different people. For example, the SNP rs324420 for the FAAH gene is associated with pain sensitivity and use of postoperative analgesia. Users with homozygous alleles (C/C) may have higher pain sensitivity to cold temperatures and more need for analgesia during periods of acute pain, such as after an operation. This information is beneficial when a provider is prescribing *cannabis* after an operation. By analyzing these SNPs, a subject at risk for developing pain or suffering from pain may be effectively treated with the formulations as disclosed herein.

Psychosis may, for example, relate to a user's propensity for becoming disconnected from reality. Psychosis from *cannabis* can cause delusions, which are strong beliefs that don't make sense and/or are not consistent with the user's actual beliefs. Research indicates that *cannabis* may have a more profound effect on users with particular genetic markers. For example, the SNP rs1130233 for the AKT1 gene is associated with the risk of psychosis-like effects (e.g., include delusion, delirium and confusion) after consuming THC. Users with heterozygous alleles (C/T) may have an increased risk of experience acute psychosis-like effects after consuming THC. In another example, the SNP rs2494732 for the AKT1 gene is associated with the risk of psychotic episode in users that consume *cannabis*. Users with homozygous alleles (T/T) may have a lower risk of experiencing psychotic disorder effects after consuming THC. In yet another example, the SNP rs6265 for the BDNF gene is associated with the onset of a psychotic disorder at a young age. Users with homozygous alleles (G/G) may not be at risk for onset psychosis if the user is already predisposed to developing psychosis. In yet another example, the SNP rs4680 for the COMT gene is also associated with psychosis-like effects (e.g., delusion, delirium, and confusion) after consuming THC. Users with homozygous alleles (A/A) may be less likely to experience psychosis-like effects after consuming THC relative to people with different genotypes. In another example, the SNP rs1076560 for the DRD2 gene is associated with a greater risk of developing psychosis (e.g., having regular hallucinations and delusions) in *cannabis* users. In yet another example, the SNP rs2494732 for the AKT1 gene is associated with a risk of a psychotic disorder and cognitive disabilities, including verbal memory and sustained attention impairments. Users with homozygous alleles (T/T) may have a lower risk of psychotic disorder and a lower risk of memory and attention impairments after consuming THC than users with a different genotype. This information may be particularly beneficial as it may prevent a user that is predisposed to psychosis from overdosing on THC. By analyzing these SNPs, a subject at risk for developing psychosis or suffering from psychosis may be effectively treated with the formulations as disclosed herein.

Psychotic like effects may, for example, include delusions and delirium caused by *cannabis* usage. Research indicates that *cannabis* use can cause schizophrenia, an illness that can cause a person to feel as if they have lost touch with reality. Research also indicates that certain genetic markers can indicate whether an individual is more likely to experience psychotic like effects when consuming *cannabis*. For example, the SNP 5-HTTLPR for the gene SLC6A4 is associated with psychotic like effects in user with bipolar disorder when that user consumes *cannabis*. By analyzing these SNPs, a subject at risk for developing psychotic like effects or suffering from psychotic like effects may be effectively treated with the formulations as disclosed herein.

Sleep quality may, for example, relate to the amount of time a user sleeps, the amount of times a user wakes up during the night, and the amount of time it takes a user to fall asleep. Research indicates certain genetic markers are related to sleep quality. For example, the SNP rs324420 for the FAAH gene is associated with poorer sleep quality among young *cannabis* users who exhibit depression symptoms. Users with homozygous alleles (C/C) may have an increased risk of poor sleep quality while using certain cannabinoid formulations. By analyzing these SNPs, a subject's sleep quality may be effectively treated and/or improved with the formulations as disclosed herein.

In an embodiment of the methods disclosed herein, when the subject is determined to have heterozygous alleles (A/C) at the rs1057910 polymorphism of the CYP2C9 gene, the subject is administered a formulation wherein the primary terpene is linalool and the secondary terpene is beta-caryophyllene, and having a CBD:THC ratio of about 18:1 to about 4:1. This polymorphism was associated with metabolism and pharmacokinetics of oral THC. THC levels immediately after pulmonary administration (smoking, vaporizing) are not highly affected by the rate of metabolism, so this polymorphism probably has little effect with these methods. No effect on CBD levels is expected since it is not AC metabolized to a significant extent by CYP2C9. The subject may feel the effects of oral THC more strongly or find that the effects last longer relative to people with the most common genotype. It is recommended that the first time the subject uses oral THC, that the subject starts at 60% of the standard dose. No change in THC dose is needed for pulmonary administration.

In an embodiment of the methods disclosed herein, when the subject is determined to have heterozygous alleles (C/T) at the rs35599367 polymorphism of the CYP3A4 gene, the subject is administered subject is administered a formulation wherein the primary terpene is linalool and the secondary terpene is beta-caryophyllene, and having a CBD:THC ratio of about 18:1 to about 4:1. This polymorphism has not directly been associated with cannabinoid metabolism in a clinical study. However, it is associated with decreased expression and activity of the CYP3A4 enzyme. Clinical studies with the CYP3A4 inhibitor ketoconazole showed that it boosts both THC and CBD levels after oromucosal dosing by approximately 2-fold. Therefore, it is very likely that this polymorphism affects THC and CBD levels after oral dosing. A subject may feel the effects of oral THC more strongly or find that the effects last longer relative to other people. It is recommended that the first time a subject uses oral THC, that the subject start with a 1.5-fold lower dose. No change in THC dose is needed for pulmonary administration.

In an embodiment of the methods disclosed herein, when the subject is determined to have heterozygous alleles (C/T) at the rs1045642 polymorphism of the ABCB1 gene, the subject is administered subject is administered a formulation wherein the primary terpene is linalool and the secondary terpene is beta-caryophyllene, and having a CBD:THC ratio of about 18:1 to about 4:1. Genetic factors are known to influence *cannabis* dependence. ABCB1 polymorphisms are known to modify drug pharmacokinetics and research studies have indicated their role in generating and maintaining *cannabis* dependence. The biomarker rs1045642 has been identified and associated with the risk of *cannabis* dependence. Research studies suggest that a subject may have a higher risk of *cannabis* dependence relative to people with the TT genotype. Any subject should consult a specialist before titrating a dose of THC. Caution is warranted.

EXAMPLES

The Examples that follow are illustrative of specific embodiments of the invention, and various uses thereof. They are set forth for explanatory purposes only, and are not to be taken as limiting the invention.

Exemplary formulations:

1. 1:1 10 mg CBD, 10 mg THC (1 mg CBN, Myrcene 5%, Terpinolene 3%)
2. 4:1 40 mg CBD, 10 mg THC (α-Pinene 5%, Terpineol 3%)
3. 1:1 10 mg CBD, 10 mg THC (Limonene 5%, Linalool 3%, 1 mg Bisabolol)
4. 1:1 10 mg CBD, 10 mg THC (13-Caryophyllene 5%, Limonene 3%)
5. 4:1 40 mg CBD, 10 mg THC (Linalool 5%, β-Caryophyllene, 1% Borneol, 1% Pinene)
6. 1:2 10 mg CBD, 20 mg THC (5% β-Caryophyllene, 3% Myrcene, 1% Humulene, 1% CBC)
7. 1:2 10 mg CBD, 20 mg THC (Limonene 5%, Pinene 3%, THCV 1%)

Additional exemplary formulations are shown in Tables 1-9.

For Tables 1-9, while the ratios and percentages remain constant, the number of milligrams for both Tetrahydrocannabinol (THC) and Cannabidiol (CBD) are variable. Because THC is the psychoactive component of these formulations, these models utilize the THC dose as the control. These models assume a defacto dose of 10 mg THC for THC-rich formulations and 1 mg THC for CBD-rich formulations. Defacto dose is assumed for individuals with normal metabolic function and without contraindications. Metabolic function can be indicated by pharmacogenomic testing and assessment of CYP-450 enzyme expression, for example. Dosing is incremental and can titrated up or down in these proportions.

TABLE 1

Exemplary formulations

| FORMULATION | EXEMPLARY CONDITION(S) | COMPOSITION |
|---|---|---|
| UNWIND | Sleep apnea, Insomnia, waking up easy | 1:1 to 1:5 CBD:THC<br>Myrcene 3.0-5.0%<br>Linalool 1.5-5.0%<br>Terpinolene 1.0-3.0%<br>0.04-0.1% Lavender<br>0.04-0.1% Chamomile<br>0.04-0.1% Sandalwood |
| FOCUS | ADHD, Autism, High energy, Anxiety, Hyperactivity | 4:1 to 20:1 CBD:THC<br>alpha Pinene 3.0-5.0%<br>Terpineol 2.0-3.0%<br>Eucalyptol 0.25-1.0%<br>0.04-0.1% Wild Orange<br>0.04-0.1% Peppermint<br>0.04-0.1% Pulegone |
| COGNITIVE | Stress, Depression | 1:1 to 20:1 - CBD:THC<br>Limonene 2.0-5.0%<br>Linalool 1.5-5.0%<br>0.5-1.5% Bisabolol<br>0.04-0.1% Juniper Berry<br>0.04-0.1% Lime<br>0.04-0.1% Lavender |
| IMMUNE | Auto-immune disorders, Pain, treatment of inflammation related symptoms | 1:1 to 1:10 - CBD:THC<br>Beta Caryophyllene 1.0-5.0%<br>Limonene 2.0-5.0%<br>0.01-5.0% BCAA (branched chain amino acids)<br>0.04-0.1% Glutamine<br>0.04-0.1% *Marjoram*<br>0.04-0.1% Ginger<br>0.04-0.1% Lemongrass |
| RESPONSE | Fatigue, Low energy, Anxiety | 4:1 to 20:1 - CBD:THC<br>Linalool 1.5-5.0%<br>Borneol 0.5-2.0%<br>Beta Caryophyllene 1.0-5.0%<br>Pinene 3.0-5.0%<br>0.04-0.1% Geranium<br>0.04-0.1% Mint<br>0.04-0.1% Guava<br>0.04-0.1% Lavender |
| RELIEF | Cancer, Pain, Inflammation | 1:1 to 1:20 - CBD:THC<br>Beta Caryophyllene 1.0-5.0%<br>Myrcene 3.0-5.0%<br>Humulene 1.0-2.0%<br>CBC 0.5-2.0%<br>0.04-0.1% Lavender<br>0.04-0.1% Sandalwood<br>0.04-0.1% Cayenne<br>0.04-0.1% Peppermint |
| ACTIVATE/WELLNESS | Mood disorders, fatigue, low energy | 1:1 to 1:20 - CBD:THC<br>Limonene 2.0-5.0%<br>Pinene 3.0-5.0%<br>THCV 0.5-2.0%<br>0.04-0.1% Peppermint<br>0.04-0.1% Eucalyptol<br>0.04-0.1% Cedarwood<br>0.04-0.1% Rosemary |
| RECOVERY | Post-workout, exercise | 1:1 to 1:3 - CBD:THC<br>BCAA 500-1500 mg<br>L-glutamine 250-750 mg<br>Pipeline 1-10 mg<br>Magnesium stearate 5-15 mg<br>MCC (Endurance) 5-15 mg<br>Silicon dioxide 4-12 mg |

OPTIONAL INGREDIENTS: Any of the above formulations may also further comprise: CBC, CBCV, CBD, CBDA, CBDV, CBG, CBGV, CBL, CBN, CBV, THC, THCA, THCV, Ocimene, Valencene, Geraniol, Theramine, Phytol, Sabinene, Isobomeol, Cedrene, Guaiol, Geranyl Acetate, Eucalyptol, Carene, Fenchol, Bisabolol, Camphene, Camphor, Menthol, Nerolidol, Isopulegol, Cymene, or Pulegone.
In certain embodiments, any of the above formulations may be essentially free of THC.

Formulation #4 Wellness 1:1-1:20

| | THC Dose (mg): | | | | | | | | | |
|---|---|---|---|---|---|---|---|---|---|---|
| | 10 | 10 | 10 | 10 | 10 | 10 | 10 | 10 | 10 | 10 |
| Ratio: | 1:1 | 1:2 | 1:3 | 1:4 | 1:5 | 1:6 | 1:7 | 1:8 | 1:9 | 1:10 |
| By Milligrams: | | | | | | | | | | |
| CBD (mg) | 10.00 | 5.00 | 3.33 | 2.50 | 2.00 | 1.67 | 1.43 | 1.25 | 1.11 | 1.00 |
| THC (mg) | 10.00 | 10.00 | 10.00 | 10.00 | 10.00 | 10.00 | 10.00 | 10.00 | 10.00 | 10.00 |
| By Percentage: | | | | | | | | | | |
| CBD (%) | 50.0% | 33.33% | 25.00% | 20.00% | 16.67% | 14.29% | 12.50% | 11.11% | 10.00% | 9.09% |
| THC (%) | 50.0% | 66.67% | 75.00% | 80.00% | 83.33% | 85.71% | 87.50% | 88.89% | 90.00% | 90.91% |
| Additional Cannabinoids, Terpenes & Active Ingredients | | | | | | | | | | |
| Beta Caryophylene | 2.50% | 2.50% | 2.50% | 2.50% | 2.50% | 2.50% | 2.50% | 2.50% | 2.50% | 2.50% |
| Limonene | 2.00% | 2.00% | 2.00% | 2.00% | 2.00% | 2.00% | 2.00% | 2.00% | 2.00% | 2.00% |
| Pinene | 1.00% | 1.00% | 1.00% | 1.00% | 1.00% | 1.00% | 1.00% | 1.00% | 1.00% | 1.00% |
| Majoram | 0.10% | 0.10% | 0.10% | 0.10% | 0.10% | 0.10% | 0.10% | 0.10% | 0.10% | 0.10% |
| Lemongrass | 0.10% | 0.10% | 0.10% | 0.10% | 0.10% | 0.10% | 0.10% | 0.10% | 0.10% | 0.10% |
| Mint | 0.10% | 0.10% | 0.10% | 0.10% | 0.10% | 0.10% | 0.10% | 0.10% | 0.10% | 0.10% |
| Ginger | 0.10% | 0.10% | 0.10% | 0.10% | 0.10% | 0.10% | 0.10% | 0.10% | 0.10% | 0.10% |

-continued

| Formulation #4 Wellness 1:1-1:20 | | | | | | | | | | |
|---|---|---|---|---|---|---|---|---|---|---|
| THC Dose (mg): | | | | | | | | | | |
| | 10 | 10 | 10 | 10 | 10 | 10 | 10 | 10 | 10 | 10 |
| Ratio: By Milligrams: | 1:11 | 1:12 | 1:13 | 1:14 | 1:15 | 1:16 | 1:17 | 1:18 | 1:19 | 1:20 |
| CBD (mg) | 0.91 | 0.83 | 0.77 | 0.71 | 0.67 | 0.63 | 0.59 | 0.56 | 0.53 | 0.50 |
| THC (mg) | 10.00 | 10.00 | 10.00 | 10.00 | 10.00 | 10.00 | 10.00 | 10.00 | 10.00 | 10.00 |
| By Percentage: | | | | | | | | | | |
| CBD (%) | 8.33% | 7.69% | 7.14% | 6.67% | 6.25% | 5.88% | 5.56% | 5.26% | 5.00% | 4.76% |
| THC (%) | 91.67% | 92.31% | 92.86% | 93.33% | 93.75% | 94.12% | 94.44% | 94.74% | 95.00% | 95.24% |
| Additional Cannabinoids, Terpenes & Active Ingredients | | | | | | | | | | |
| Beta Caryophylene | 2.50% | 2.50% | 2.50% | 2.50% | 2.50% | 2.50% | 2.50% | 2.50% | 2.50% | 2.50% |
| Limonene | 2.00% | 2.00% | 2.00% | 2.00% | 2.00% | 2.00% | 2.00% | 2.00% | 2.00% | 2.00% |
| Pinene | 1.00% | 1.00% | 1.00% | 1.00% | 1.00% | 1.00% | 1.00% | 1.00% | 1.00% | 1.00% |
| Majoram | 0.10% | 0.10% | 0.10% | 0.10% | 0.10% | 0.10% | 0.10% | 0.10% | 0.10% | 0.10% |
| Lemongrass | 0.10% | 0.10% | 0.10% | 0.10% | 0.10% | 0.10% | 0.10% | 0.10% | 0.10% | 0.10% |
| Mint | 0.10% | 0.10% | 0.10% | 0.10% | 0.10% | 0.10% | 0.10% | 0.10% | 0.10% | 0.10% |
| Ginger | 0.10% | 0.10% | 0.10% | 0.10% | 0.10% | 0.10% | 0.10% | 0.10% | 0.10% | 0.10% |

| Formulation #2 Focus 20:1-1:1 | | | | | | | | | | |
|---|---|---|---|---|---|---|---|---|---|---|
| THC Dose (mg): | | | | | | | | | | |
| | 1 | 1 | 1 | 1 | 1 | 1 | 1 | 1 | 1 | 1 |
| Ratio: By Milligrams: | 20:1 | 19:1 | 18:1 | 17:1 | 16:1 | 15:1 | 14:1 | 13:1 | 12:1 | 11:1 |
| CBD (mg) | 20.00 | 19.00 | 18.00 | 17.00 | 16.00 | 15.00 | 14.00 | 13.00 | 12.00 | 11.00 |
| THC (mg) | 1.00 | 1.00 | 1.00 | 1.00 | 1.00 | 1.00 | 1.00 | 1.00 | 1.00 | 1.00 |
| By Percentage: | | | | | | | | | | |
| CBD (%) | 95.24% | 95.00% | 94.74% | 94.44% | 94.12% | 93.75% | 93.35% | 92.86% | 92.31% | 91.67% |
| THC (%) | 4.76% | 5.00% | 5.26% | 5.56% | 5.88% | 6.25% | 6.67% | 7.14% | 7.69% | 8.33% |
| Additional Cannabinoids, Terpenes & Active Ingredients | | | | | | | | | | |
| Terpenelene | 2.00% | 2.00% | 2.00% | 2.00% | 2.00% | 2.00% | 2.00% | 2.00% | 2.00% | 2.00% |
| Eucolyptol | 0.50% | 0.50% | 0.50% | 0.50% | 0.50% | 0.50% | 0.50% | 0.50% | 0.50% | 0.50% |
| Pinene | 3.00% | 3.00% | 3.00% | 3.00% | 3.00% | 3.00% | 3.00% | 3.00% | 3.00% | 3.00% |
| Wild Orange | 0.10% | 0.10% | 0.10% | 0.10% | 0.10% | 0.10% | 0.10% | 0.10% | 0.10% | 0.10% |
| Pulegone | 0.10% | 0.10% | 0.10% | 0.10% | 0.10% | 0.10% | 0.10% | 0.10% | 0.10% | 0.10% |
| Cayenne | 0.10% | 0.10% | 0.10% | 0.10% | 0.10% | 0.10% | 0.10% | 0.10% | 0.10% | 0.10% |
| Peppermint | 0.10% | 0.10% | 0.10% | 0.10% | 0.10% | 0.10% | 0.10% | 0.10% | 0.10% | 0.10% |
| THC Dose (mg): | | | | | | | | | | |
| | 1 | 1 | 1 | 1 | 1 | 1 | 1 | 1 | 1 | 1 |
| Ratio: By Milligrams: | 10:1 | 9:1 | 8:1 | 7:1 | 6:1 | 5:1 | 4:1 | 3:1 | 2:1 | 1:1 |
| CBD (mg) | 10.00 | 9.00 | 8.00 | 7.00 | 6.00 | 5.00 | 4.00 | 3.00 | 2.00 | 10.00 |
| THC (mg) | 1.00 | 1.00 | 1.00 | 1.00 | 1.00 | 1.00 | 1.00 | 1.00 | 1.00 | 10.00 |

Formulation #2
Focus 20:1-1:1

By Percentage:

| | | | | | | | | | | |
|---|---|---|---|---|---|---|---|---|---|---|
| CBD (%) | 90.91% | 90.00% | 88.89% | 87.50% | 85.71% | 83.33% | 80.00% | 75.00% | 66.67% | 50.00% |
| THC (%) | 9.09% | 10.00% | 11.11% | 12.50% | 14.29% | 16.67% | 20.00% | 25.00% | 33.33% | 50.00% |

Additional Cannabinoids, Terpenes & Active Ingedients

| | | | | | | | | | | |
|---|---|---|---|---|---|---|---|---|---|---|
| Terpenelene | 2.00% | 2.00% | 2.00% | 2.00% | 2.00% | 2.00% | 2.00% | 2.00% | 2.00% | 2.00% |
| Eucolyptol | 0.50% | 0.50% | 0.50% | 0.50% | 0.50% | 0.50% | 0.50% | 0.50% | 0.50% | 0.50% |
| Pinene | 3.00% | 3.00% | 3.00% | 3.00% | 3.00% | 3.00% | 3.00% | 3.00% | 3.00% | 3.00% |
| Wild Orange | 0.10% | 0.10% | 0.10% | 0.10% | 0.10% | 0.10% | 0.10% | 0.10% | 0.10% | 0.10% |
| Pulegone | 0.10% | 0.10% | 0.10% | 0.10% | 0.10% | 0.10% | 0.10% | 0.10% | 0.10% | 0.10% |
| Cayenne | 0.10% | 0.10% | 0.10% | 0.10% | 0.10% | 0.10% | 0.10% | 0.10% | 0.10% | 0.10% |
| Peppermint | 0.10% | 0.10% | 0.10% | 0.10% | 0.10% | 0.10% | 0.10% | 0.10% | 0.10% | 0.10% |

TABLE 4

Formulation #1
Unwind 1:1-1:5

| | | | | | |
|---|---|---|---|---|---|
| THC Dose (mg): | 10 | 10 | 10 | 10 | 10 |
| Ratio: | 1:1 | 1:2 | 1:3 | 1:4 | 1:5 |
| By Milligrams: | | | | | |
| CBD (mg) | 10.00 | 5.80 | 3.33 | 2.50 | 2.00 |
| THC (mg) | 10.00 | 10.00 | 10.00 | 10.00 | 10.00 |
| By percentage: | | | | | |
| CBD (%) | 50.00% | 33.33% | 25.00% | 20.00% | 16.67% |
| THC (%) | 50.00% | 66.67% | 75.00% | 80.00% | 83.33% |
| Additional Cannabinoids, Terpenes & Active Ingredients | | | | | |
| Myecene | 3.50% | 3.50% | 3.50% | 3.50% | 3.50% |
| Linalool | 1.50% | 1.50% | 1.50% | 1.50% | 1.50% |
| Terpenolene | 2.50% | 2.50% | 2.50% | 2.50% | 2.50% |
| Lavender | 0.10% | 0.10% | 0.10% | 0.10% | 0.10% |
| Chamomile | 0.10% | 0.10% | 0.10% | 0.10% | 0.10% |
| Sandlewood | 0.10% | 0.10% | 0.10% | 0.10% | 0.10% |

TABLE 5

Formulation #3
Cognitive 20:1-2:1

| | | | | | | | | | | |
|---|---|---|---|---|---|---|---|---|---|---|
| THC Dose (mg): | 1 | 1 | 1 | 1 | 1 | 1 | 1 | 1 | 1 | 1 |
| Ratio: | 20:1 | 19:1 | 18:1 | 17:1 | 16:1 | 15:1 | 14:1 | 13:1 | 12:1 | 11:1 |
| By Milligrams: | | | | | | | | | | |
| CBD (mg) | 20.00 | 19.00 | 18.00 | 17.00 | 16.00 | 15.00 | 14.00 | 13.00 | 12.00 | 11.00 |
| THC (mg) | 1.00 | 1.00 | 1.00 | 1.00 | 1.00 | 1.00 | 1.00 | 1.00 | 1.00 | 1.00 |
| By Percentage: | | | | | | | | | | |
| CBD (%) | 95.24% | 95.00% | 94.74% | 94.44% | 94.12% | 93.75% | 93.35% | 92.86% | 92.31% | 91.67% |
| THC (%) | 4.76% | 5.00% | 5.26% | 5.56% | 5.88% | 6.25% | 6.67% | 7.14% | 7.69% | 8.33% |

Additional Cannabinoids, Terpenes & Active Ingredients

| | | | | | | | | | | |
|---|---|---|---|---|---|---|---|---|---|---|
| Linalool | 2.00% | 2.00% | 2.00% | 2.00% | 2.00% | 2.00% | 2.00% | 2.00% | 2.00% | 2.00% |
| Limocene | 3.50% | 3.50% | 3.50% | 3.50% | 3.50% | 3.50% | 3.50% | 3.50% | 3.50% | 3.50% |
| Bisabolol | 1.00% | 1.00% | 1.00% | 1.00% | 1.00% | 1.00% | 1.00% | 1.00% | 1.00% | 1.00% |
| Lime | 0.10% | 0.10% | 0.10% | 0.10% | 0.10% | 0.10% | 0.10% | 0.10% | 0.10% | 0.10% |
| Junniper Berry | 0.10% | 0.10% | 0.10% | 0.10% | 0.10% | 0.10% | 0.10% | 0.10% | 0.10% | 0.10% |
| Mint | 0.10% | 0.10% | 0.10% | 0.10% | 0.10% | 0.10% | 0.10% | 0.10% | 0.10% | 0.10% |
| Guava | 0.10% | 0.10% | 0.10% | 0.10% | 0.10% | 0.10% | 0.10% | 0.10% | 0.10% | 0.10% |
| Lavender | 0.10% | 0.10% | 0.10% | 0.10% | 0.10% | 0.10% | 0.10% | 0.10% | 0.10% | 0.10% |

TABLE 5-continued

Formulation #3
Cognitive 20:1-2:1

| | THC Dose (mg): | | | | | | | | |
|---|---|---|---|---|---|---|---|---|---|
| | 1 | 1 | 1 | 1 | 1 | 1 | 1 | 1 | 1 |
| Ratio:<br>By Milligrams: | 10:1 | 9:1 | 8:1 | 7:1 | 6:1 | 5:1 | 4:1 | 3:1 | 2:1 |
| CBD (mg) | 10.00 | 9.00 | 8.00 | 7.00 | 6.00 | 5.00 | 4.00 | 3.00 | 2.00 |
| THC (mg) | 1.00 | 1.00 | 1.00 | 1.00 | 1.00 | 1.00 | 1.00 | 1.00 | 1.00 |
| By Percentage: | | | | | | | | | |
| CBD (%) | 90.91% | 90.00% | 88.89% | 87.50% | 85.71% | 83.33% | 80.00% | 75.00% | 66.67% |
| THC (%) | 9.09% | 10.00% | 11.11% | 12.50% | 14.29% | 16.67% | 20.00% | 25.00% | 33.33% |
| Additional Cannabinoids, Terpenes & Active Ingredients | | | | | | | | | |
| Linalool | 2.00% | 2.00% | 2.00% | 2.00% | 2.00% | 2.00% | 2.00% | 2.00% | 2.00% |
| Limocene | 3.50% | 3.50% | 3.50% | 3.50% | 3.50% | 3.50% | 3.50% | 3.50% | 3.50% |
| Bisabolol | 1.00% | 1.00% | 1.00% | 1.00% | 1.00% | 1.00% | 1.00% | 1.00% | 1.00% |
| Lime | 0.10% | 0.10% | 0.10% | 0.10% | 0.10% | 0.10% | 0.10% | 0.10% | 0.10% |
| Junniper Berry | 0.10% | 0.10% | 0.10% | 0.10% | 0.10% | 0.10% | 0.10% | 0.10% | 0.10% |
| Mint | 0.10% | 0.10% | 0.10% | 0.10% | 0.10% | 0.10% | 0.10% | 0.10% | 0.10% |
| Guava | 0.10% | 0.10% | 0.10% | 0.10% | 0.10% | 0.10% | 0.10% | 0.10% | 0.10% |
| Lavender | 0.10% | 0.10% | 0.10% | 0.10% | 0.10% | 0.10% | 0.10% | 0.10% | 0.10% |

TABLE 6

Formulation #6
Response 18:1-4:1

| | THC Dose (mg): | | | | | | | |
|---|---|---|---|---|---|---|---|---|
| | 1 | 1 | 1 | 1 | 1 | 1 | 1 | 1 |
| Ratio:<br>By Milligrams: | 18:1 | 17:1 | 16:1 | 15:1 | 14:1 | 13:1 | 12:1 | 11:1 |
| CBD (mg) | 18.00 | 17.00 | 16.00 | 15.00 | 14.00 | 13.00 | 12.00 | 11.00 |
| THC (mg) | 1.00 | 1.00 | 1.00 | 1.00 | 1.00 | 1.00 | 1.00 | 1.00 |
| By Percentage: | | | | | | | | |
| CBD (%) | 94.74% | 94.44% | 94.12% | 93.75% | 93.33% | 92.86% | 92.31% | 91.67% |
| THC (%) | 5.26% | 5.56% | 5.88% | 6.25% | 6.67% | 7.14% | 7.69% | 8.33% |
| Additional Cannabinoids, Terpenes & Active Ingredients | | | | | | | | |
| Linalool | 3.50% | 3.50% | 3.50% | 3.50% | 3.50% | 3.50% | 3.50% | 3.50% |
| Terpenolene | 1.00% | 1.00% | 1.00% | 1.00% | 1.00% | 1.00% | 1.00% | 1.00% |
| Borneol | 2.00% | 2.00% | 2.00% | 2.00% | 2.00% | 2.00% | 2.00% | 2.00% |
| Mint | 0.10% | 0.10% | 0.10% | 0.10% | 0.10% | 0.10% | 0.10% | 0.10% |
| Guarava | 0.10% | 0.10% | 0.10% | 0.10% | 0.10% | 0.10% | 0.10% | 0.10% |
| Lavender | 0.04% | 0.04% | 0.04% | 0.04% | 0.04% | 0.04% | 0.04% | 0.04% |

| | THC Dose (mg): | | | | | | |
|---|---|---|---|---|---|---|---|
| | 1 | 1 | 1 | 1 | 1 | 1 | 1 |
| Ratio:<br>By Milligrams: | 10:1 | 9:1 | 8:1 | 7:1 | 6:1 | 5:1 | 4:1 |
| CBD (mg) | 10.00 | 9.00 | 8.00 | 7.00 | 6.00 | 5.00 | 4.00 |
| THC (mg) | 1.00 | 1.00 | 1.00 | 1.00 | 1.00 | 1.00 | 1.00 |
| By Percentage: | | | | | | | |
| CBD (%) | 90.91% | 90.00% | 88.89% | 87.50% | 85.71% | 83.33% | 80.00% |
| THC (%) | 9.09% | 10.00% | 11.11% | 12.50% | 14.29% | 16.67% | 20.00% |

TABLE 6-continued

Formulation #6
Response 18:1-4:1

| Additional Cannabinoids, Terpenes & Active Ingredients | | | | | | | |
|---|---|---|---|---|---|---|---|
| Linalool | 3.50% | 3.50% | 3.50% | 3.50% | 3.50% | 3.50% | 3.50% |
| Terpenolene | 1.00% | 1.00% | 1.00% | 1.00% | 1.00% | 1.00% | 1.00% |
| Borneol | 2.00% | 2.00% | 2.00% | 2.00% | 2.00% | 2.00% | 2.00% |
| Mint | 0.10% | 0.10% | 0.10% | 0.10% | 0.10% | 0.10% | 0.10% |
| Guarava | 0.10% | 0.10% | 0.10% | 0.10% | 0.10% | 0.10% | 0.10% |
| Lavender | 0.04% | 0.04% | 0.04% | 0.04% | 0.04% | 0.04% | 0.04% |

TABLE 7

Formulation #7
Relief 1:1-1:6

| | THC Dose (mg): | | | | | |
|---|---|---|---|---|---|---|
| | 10 | 10 | 10 | 10 | 10 | 10 |
| Ratio: | 1:1 | 1:2 | 1:3 | 1:4 | 1:5 | 1:6 |
| By Milligrams: | | | | | | |
| CBD (mg) | 10.00 | 5.00 | 3.33 | 2.50 | 2.00 | 1.67 |
| THC (mg) | 10.00 | 10.00 | 10.00 | 10.00 | 10.00 | 10.00 |
| By Percentage: | | | | | | |
| CBD (%) | 50.00% | 33.33% | 25.00% | 20.00% | 16.67% | 14.29% |
| THC (%) | 50.00% | 66.67% | 75.00% | 80.00% | 83.33% | 85.71% |
| Additional Cannabinoids, Terpenes & Active Ingredients | | | | | | |
| Myrcene | 2.00% | 2.00% | 2.00% | 2.00% | 2.00% | 2.00% |
| Beta Caryophyllene | 3.50% | 3.50% | 3.50% | 3.50% | 3.50% | 3.50% |
| Humulene | 1.00% | 1.00% | 1.00% | 1.00% | 1.00% | 1.00% |
| Lavender | 0.10% | 0.10% | 0.10% | 0.10% | 0.10% | 0.10% |
| Sandlewood | 0.10% | 0.10% | 0.10% | 0.10% | 0.10% | 0.10% |
| Pepperming | 0.10% | 0.10% | 0.10% | 0.10% | 0.10% | 0.10% |
| Rosemary | 0.10% | 0.10% | 0.10% | 0.10% | 0.10% | 0.10% |

TABLE 8

Formulation #5
IMMUNE 1:1-1:10

| | THC Dose (mg): | | | | | | | | | |
|---|---|---|---|---|---|---|---|---|---|---|
| | 10 | 10 | 10 | 10 | 10 | 10 | 10 | 10 | 10 | 10 |
| Ratio: | 1:1 | 1:2 | 1:3 | 1:4 | 1:5 | 1:6 | 1:7 | 1:8 | 1:9 | 1:10 |
| By Milligrams: | | | | | | | | | | |
| CBD (mg) | 10.00 | 5.00 | 3.33 | 2.50 | 2.00 | 1.67 | 1.43 | 1.25 | 1.11 | 1.00 |
| THC (mg) | 10.00 | 10.00 | 10.00 | 10.00 | 10.00 | 10.00 | 10.00 | 10.00 | 10.00 | 10.00 |
| By Percentage: | | | | | | | | | | |
| CBD (%) | 50.00% | 33.33% | 25.00% | 20.00% | 16.67% | 14.29% | 12.50% | 11.11% | 10.00% | 9.09% |
| THC (%) | 50.00% | 66.67% | 75.00% | 80.00% | 83.33% | 85.71% | 87.50% | 88.89% | 90.00% | 90.91% |
| Additional Cannabinoids, Terpenes & Active Ingredients | | | | | | | | | | |
| Beta Caryophyllene | 3.00% | 3.00% | 3.00% | 3.00% | 3.00% | 3.00% | 3.00% | 3.00% | 3.00% | 3.00% |
| Humulene | 2.00% | 2.00% | 2.00% | 2.00% | 2.00% | 2.00% | 2.00% | 2.00% | 2.00% | 2.00% |
| Terpenolene | 1.00% | 1.00% | 1.00% | 1.00% | 1.00% | 1.00% | 1.00% | 1.00% | 1.00% | 1.00% |
| Lavender | 0.10% | 0.10% | 0.10% | 0.10% | 0.10% | 0.10% | 0.10% | 0.10% | 0.10% | 0.10% |
| Chamomile | 0.10% | 0.10% | 0.10% | 0.10% | 0.10% | 0.10% | 0.10% | 0.10% | 0.10% | 0.10% |
| Sandlewood | 0.10% | 0.10% | 0.10% | 0.10% | 0.10% | 0.10% | 0.10% | 0.10% | 0.10% | 0.10% |

TABLE 9

Formulation #8
Recovery (Capsules)
This product is a powder-based and encapsulated for oral administration

| | |
|---|---|
| Vegan Branch Chain Amino Acids, (L-Leucine, L-Isoleuice, L-Valline) | 1,000 mg |
| L-Glutamine | 500 mg |
| BioPerine | 5 mg |
| Magnesium Stearate | 10 mg |
| MCC (Endurance) | 10 mg |
| Silicon Dioxide (Sipernat22S) | 8 mg |
| CBD/THC dose/ratio: | |
| Hemp Extract (CBD) 5.5 mg | 5.5 mg |
| THC Isolate Powder 2.5 mg | 2.5 mg |

TABLE 10

Single-nucleotide polymorphisms (SNPs), endocannabinoid genotype, and potential formulation.

| SNIP I.D. | Gene | rsID | Category | Formulation | Effect/Findings/Discussion | References (PMID) |
|---|---|---|---|---|---|---|
| 2-01-AFMLG | ABCB1 | rs1045642 | Response to Cannabinoids | RESPONSE | When consumed regularly, THC can accumulate in your body. If for example, you are a T carrier, and you stop consuming for a significant period of time, you may have higher levels of THC for an extended period of time. You may find withdrawal easier than the other genotypes (C carrier) because you may excrete THC more slowly. It is important to note that this polymorphism is only one of many contributing factors to withdrawal experiences. | 28917442 |
| 3-01-A | AKT1 | rs1130233 | Response to Cannabinoids | COGNITIVE | This polymorphism is associated with the risk of psychotomimetic (psychosis-like) effects after consuming THC. The risk is especially increased by an interaction with the SLC6A3 3'UTR VNTR polymorphism (9 repeat allele). It is important to note that this polymorphism is only one of many contributing factors to this side effect. | 22290123 |
| 4-01-A | AKT1 | rs1130233 | Response to Cannabinoids | COGNITIVE | Impaired motor control can be caused by THC, but this effect is modulated by this polymorphism. It is important to note that this polymorphism is only one of many contributing factors to this profile. | 25065544 |
| 5-01-2AL | AKT1 | rs2494732 | Response to Cannabinoids | COGNITIVE | This polymorphism may confer a significantly elevated risk of a psychotic disorder for those who use cannabis -- and when some previous psychosis of some sort is present, cannabis may dramatically increase further psychotic experiences. However, this polymorphism is only one of many contributing factors to this profile. | 22831980 |
| 6-01-2AL | AKT1 | rs2494732 | Response to Cannabinoids | COGNITIVE | Cognitive functioning, including attention and accuracy, are adversely affected by THC. This effect may be modified by this AKT1 polymorphisms and by interactions with psychosis. It is important to note that polymorphism is | 21775978 |

TABLE 10-continued

Single-nucleotide polymorphisms (SNPs), endocannabinoid genotype, and potential formulation.

| | | | | | | |
|---|---|---|---|---|---|---|
| 7-01-2AL | AKT1 | rs2494732 | Response to Cannabinoids | COGNITIVE | only one of many contributing factors to this profile. THC can cause acute psychotomimetic (psychosis-like) effects in some people and this response is modulated by this AKT1 polymorphism. It is important to note that this polymorphism is only one of many contributing factors to this profile. | 26882038 |
| 8-01-2AL | AKT1 | rs2494732 | Response to Cannabinoids | COGNITIVE | This polymorphism was associated with greater risk of developing psychosis in cannabis risers. It is important to note that this polymorphism is only one of many contributing factors to this profile. | 27336035; PMC4849451 |
| 9-01-ALG | BDNF | rs6265 | Response to Cannabinoids | RESPONSE | Cannabis use was associated with earlier age of onset of a psychotic disorder. In one study, this effect was stronger with a higher frequency of cannabis use and earlier age at first use. In males, this effect occured independent of BDNF genotype. In females, the effect of cannabis use on age of onset of psychosis was highly dependent on this polymorphism. It is important to note that this polymorphism is only one of many contributing factors to this profile. | 21305693 |
| | CNR1 | (rs202329, rs1535255, rs806379) | Response to Cannabinoids | COGNITIVE | Based on your TAG haplotype of ACA, you may have a higher risk of experiencing acute psychomimetic effects after consumption of THC. [In exploring CNR1, AKT1, BDNF and COMT genes with psychotomimetic effects when first using cannabis (PEFU), Reserchers found a significant association with a functional haplotype block in CNR1], (Overall reccomendation include not consuming alcohol and other substances in parallel with THC use). Consult a specialist for a dose titration/ adjustment. It is important to note that this polymorphism is only one of many contributing factors to this profile. | 24445906 |
| 16-01-2AFML | CNR1 | rs1049353 | Response to Cannabinoids | COGNITIVE | This polymorphism was associated with performance on a test of executive function (mental skills that help you set and accomplish goals) and sustained attention in a combined group of cannabis users and non-users. It is important to note that this is only one of many factors determining on how you sustain attention and focus on activities. | roar.uel.ac.uk/4985/1/ Stephanie%20Marie%20Lynch.pdf |

TABLE 10-continued

Single-nucleotide polymorphisms (SNPs), endocannabinoid genotype, and potential formulation.

| | | | | | | |
|---|---|---|---|---|---|---|
| 17-01-AFM | CNR1 | rs1406977 | Response to Cannabinoids | COGNITIVE | This polymorphism was associated with performance on a working memory task in cannabis users, but not in non-cannabis users. It is important to note that this is only one of many factors determining your working memory profile. | 25139064; 27261878 |
| 26-01-2 | COMT | rs4680 | Response to Cannabinoids | COGNITIVE | This polymorphism was associated with the onset of psychotomimetic (psychosis-like) effects after consuming THC. However, this was not confirmed by all studies. Other studies found an interacting effect of childhood abuse or psychosis-related cognitive changes. It is important to note that this polymorphism is only one of many contributing factors to this profile. | 21947654; 23445265; 26464454; 16936704 |
| 27-01-2 | COMT | rs4680 | Response to Cannabinoids | COGNITIVE | This polymorphism was associated with the volume/neuroanatomical changes of specific brain regions in young males who are chronic cannabis users. These include the ventral caudate nucleus (involved in memory), the left amygdala (involved in emotions such as anxiety), prefrontal cortex, neostriatum (caudate-putamen), ACC and the hippocampus-amygdala complex (respectively tied into short-term memory emotions, moods, and other functions related to depression and anxiety). It is important to note that this is only one of many factors that could be linked to anxiety and other emotions. | 23311613 |
| 28-01-2 | COMT | rs4680 | Response to Cannabinoids | COGNITIVE | This polymorphism was associated with memory and other cognitive impairments after consuming THC. It is important to note that this polymorphism is only one of many contributing factors to this profile. | 26882038; 16936704; 26464454; 23449176 |
| 29-01-2 | COMT | rs4680 | Response to Cannabinoids | RESPONSE | Individuals who carried high function COMT and low-function DRD4 7R alleles (a combination expected to be associated with higher risk) showed more lifetime cannabis abuse in a cohort of women with binge-purge eating disorders. | 26950642 |
| 30-01-2AFMLG | CYP2C9 | rs1057910 | Response to Cannabinoids | RESPONSE | This polymorphism was associated with metabolism and pharmacokinetics of oral THC. THC levels immediately after pulmonary administration (smoking, vaporizing) are not highly affected by the rate of metabolism, so this polymorphism probably has little effect with these | 19005461 |

TABLE 10-continued

Single-nucleotide polymorphisms (SNPs), endocannabinoid genotype, and potential formulation.

| | | | | | | |
|---|---|---|---|---|---|---|
| 31-01 | CYP3A4 | rs35599367 | Response to Cannabinoids | RESPONSE | methods. No effect on CBD levels is expected since it is not metabolized to a significant extent by CYP2C9.<br>This polymorphism was associated with activity of the CYP3A4 enzyme, which can metabolize both THC and CBD. Although this polymorphism has not directly been associated with cannabinoid metabolism, clinical studies of the CYP3A4 inhibitor ketoconazole showed that it boosts both THC and CBD levels after oronmcosal dosing by approximately 2-fold. Therefore, it is likely that this polymorphism affects THC and CBD levels after oral dosing. | 23750331 |
| 32-01 | DAT1 | VNTR | Response to Cannabinoids | COGNITIVE | Genetic Factors are a key component in how your body responds to THC and CBD by way of absorption, distribution, metabolism, and excretion. The hippocampus is a brain region associated with learning, memory, and emotions. Although cannabis use was associated with a decreased volume of the hippocampus, the effect was highly dependent on this polymorphism. It is important to note that this polymorphism is only one of many contributing factors to this profile. | 29404409 |
| 33-01 | DBH | rs1611115 | Response to Cannabinoids | COGNITIVE | This polymorphism was associated with impulsivity after cannabis consumption in a group of people that regularly used cannabis and cocaine. It is important to note that this polymorphism is only one of many contributing factors to this profile. | 26667034 |
| 34-01-2AFMLG | DRD2 | rs1076560 | Response to Cannabinoids | COGNITIVE | This polymorphism was associated with greater risk of developing psychosis in cannabis users. It is important to note that this polymorphism is only one of many contributing factors to this profile. | 27336035 |
| 41-01 | FAAH | rs324420 | Response to Cannabinoids | RESPONSE | This polymorphism was associated with brain white matter integrity in young cannabis users. Lower white matter integrity was linked to apathy and depression. It is important to note that this polymorphism is only one of many contributing factors to this profile. | 26106535 |
| 42-01 | MAPK14 | rs12199654 | Response to Cannabinoids | COGNITIVE | This polymorphism was associated with white matter volume reduction in cannabis-dependent schizophrenic patients. White matter is important for cognition and executive | 22850347 |

TABLE 10-continued

Single-nucleotide polymorphisms (SNPs), endocannabinoid genotype, and potential formulation.

| | | | | | | |
|---|---|---|---|---|---|---|
| | | | | | control (e.g. attention and planning). It is important to note that this polymorphism is only one of many contributing factors to this profile. | |
| 46-01 | NRG1 | rs22153 3 | Response to Cannabinoids | COGNITIVE | This polymorphism was associated with some symptoms of schizotypal personality. It is important to note that this polymorphism is only one of many contributing factors to this profile. | roar.uel.ac.uk/4985/1/Stephanie%20Marie%20Lynch.pdf |
| 47-01 | NRG1 | rs7834206 | Response to Cannabinoids | COGNITIVE | This polymorphism was associated with deficits in auditory information processing after cannabis consumption. Auditor information processing deficits are associated with schizophrenia. It is important to note that this polymorphism is only one of many contributing factors to this profile. | 20582876 |
| 50-01 | SLC6A3 | rs28363170 | Response to Cannabinoids | COGNITIVE | This polymorphism was associated with the risk of psychotomimetic (psychosis-like) effects after consuming THC. The risk was especially increased by an interaction with the AKT1 rs1130233 polymorphism. It is important to note that this polymorphism is only one of many contributing factors to this profile. | 22290123 |
| 51-01 | SLC6A3 | rs28363170 | Response to Cannabinoids | COGNITIVE | This polymorphism was associated with the risk of psychotomimetic (psvchosis-like) effects after consuming THC. There was a further interaction of this polymorphisms with the AKT1 rs130233 polymorphism. The psychotomimetic effects of THC may be especially increased in subjects who carry both the risk alleles. Furthermore, this effect involves an alteration in the neural response to THC in the dopamine-rich regions of striatum and midbrain, consistent w ith independent evidence that the psychotomimetic effects of cannabis are mediated by dopamine. It is important to note that this polymorphism is only one of many contributing factors to this profile. | 22290123 |
| 52-01 | SLC6A4 | 5-HTTLPR | Response to Cannabinoids | COGNITIVE | This polymorphism is associated with the development of anxiety following cannabis use in adolescents. Research indicates that cannabis use is associated with an increase in symptoms of anxiety but only in carriers of the short allele of the 5-HTTLPR polymorphism. It is important to note that this polymorphism is only one of | 26860734 |

TABLE 10-continued

Single-nucleotide polymorphisms (SNPs), endocannabinoid genotype, and potential formulation.

| | | | | | | |
|---|---|---|---|---|---|---|
| 53-01 | SLC6A4 | 5-HTTLPR | Response to Cannabinoids | COGNITIVE | many contributing factors to this profile. This polymorphism was associated with psychotic symptoms in patients with bipolar disorder. The short allele of the 5-HTTLPR polymorphism of the 5-HTT gene was associated with psychotic symptoms when when there was a dependence or abuse of cannabis. It is important to note that this polymorphism is only one of many contributing factors to this profile. | 20434316 |
| 54-01 | SLC6A4 | 5-HTTLPR | Response to Cannabinoids | COGNITIVE | This polymorphism was associated with decision making abilities in a manner dependence on both genotype and cannabis use. Among youth with two "short" alleles of the 5-HTTLPR polymorphism, decision making abilities were significantly worse in cannabis users. Decision making ability was similar in cannabis users and non-users of other genotypes. It is important to note that this polymorphism is only one of many contributing factors to this profile. | 23449176 |
| | CNR1 | (AAT)n microsatellite | Physical Health & Wellness | IMMUNE | This polymorphism was associated with Irritable Bowel Syndrome (IBS) and severity of symptoms in patients with IBS. Hence, research supports the hypothesis that cannabinoid receptors may play a role in control of colonic transit and sensation in humans. It is important to note that this polymorphism is only one of many contributing factors to this profile. | 23306084; 24444427 |
| 20-01-AFM | CNR1 | rs806366 | Physical Health & Wellness | RELIEF | Migraines and its symptoms may be exacerbated by recent stressful life events. Tliis polymorphism was associated with headache with nausea only in those people who had experienced recent stressful events. It is important to note that this is only one of many factors determining whether and how you may experience migraine symptoms. | 27762084 |
| 39-01 | FAAH | rs324420 | Physical Health & Wellness | RESPONSE | This polymorphism was associated with cold pain sensitivity and use of postoperative analgesia. It is important to note that this polymorphism is only one of many contributing factors to this profile. | 26808012 |
| 40-01 | FAAH | rs324420 | Physical Health & Wellness | RESPONSE | Some opioid effects are potentiated by cannabinoids, including the endocannabinoid anandamide. This polymorphism lias been linked to the severity of morphine side effects, such | 25558980; 27977335 |

TABLE 10-continued

Single-nucleotide polymorphisms (SNPs), endocannabinoid genotype, and potential formulation.

| | | | | | | |
|---|---|---|---|---|---|---|
| | | | | | as respiratory depression and nausea/vomiting. in children and adolescents following surgery. It is important to note that this polymorphism is only one of many contributing factors to this profile. | |
| 11-01-2AFML | CNR1 | rs1049353 | Mental Health & Wellness | COGNITIVE | This polymorphism was associated with signs of post-traumatic threat symptoms. In particular, minor An allele carrier w ho also scored high on a measure of early child hood trauma reported greater threat symptoms and hypervigilance reactions. The association depends on the level of childhood physical abuse experienced. It is important to note that this polymorphism is only one of many factors contributing to the development these kind of symptoms. | 26717543 |
| 12-01-2AFML | CNR1 | rs1049353 | Mental Health & Wellness | COGNITIVE | A polymorphism in the endocannabinoid system was linked to the antidepressant responses for a class of antidepressants called selective serotonin reuptake inhibitors (SSRIs). Specifically, the C/C genotype of this CNR1 polymorphism was associated with a better response to the antidepressant citalopram/ Celexa* in males. It is important to note that this polymorphism is only one of many contributing factors to this profile. | 22826533 |
| 13-01-2AFML | CNR1 | rs1049353 | Mental Health & Wellness | COGNITIVE | The endocannabinoid signaling system (ECS) helps controls neural development, particularly during adolescence. The ECS is vulnerable to disturbances during this time (including exposure to exogenous cannabinoids) and disturbances may lead to impairments in self control. In one study of communities at risk for extra stressors, this polymorphism was linked to adolescent impulsivity following early psychosocial adversity. In particular, early adversity is linked to enhanced impulsivity among homozygous carriers of the rs806379 A and the rs1049353 T allele when compared to homozygous carriers of the respective major allele. It is important to note that this polymorphism is only one of many contributing factors to this profile. | 24980155 |
| 14-01-2AFML | CNR1 | rs1049353 | Mental Health & Wellness | COGNITIVE | The theta wave is a type of brain wave measured by EEG that is correlated with working memory | 25116250 |

TABLE 10-continued

Single-nucleotide polymorphisms (SNPs), endocannabinoid genotype, and potential formulation.

| | | | | | | |
|---|---|---|---|---|---|---|
| 15-01-2AFML | CNR1 | rs1049353 | Mental Health & Wellness | COGNITIVE | performance. This polymorphism was associated with the magnitude of the theta wave. It is important to note that this polymorphism is only one of many contributing factors to tlris profile. Tliis polymorphism was associated with the recognition of negative emotions in adolescents and the activation of associated brain areas that process emotional recognition. These brain areas include the insula and amygdala. Specifically, adolescent C/C carriers of this polymorphism had greater insula and amygdala activation of viewing angry faces.This is part of a larger body of research on how complex social cues are learned. Researchers note that this overlaps with the endocannabinoid system modulating the mesolimbic dopaminergic system. It is important to note that this polymorphism is only one of many contributing factors to tliis profile. | 26527537 |
| 19-01-AFMG | CNR1 | rs2023239 | Mental Health & Wellness | COGNITIVE | This polymorphism was associated with depression in a population of patients on methadone maintenance. For those with the C allele there are some indications of a protective role against major depressive disorder (MDD). This polymorphism is only one of many factors contributing to the development of depression. | 26331953 |
| 21-01-AFLG | CNR1 | rs806377 | Mental Health & Wellness | COGNITIVE | In one study, it was found that C allele carriers of this CNR1 polymorphism have an increased subjective happiness levels, including experiencing more overall happiness in life and experiencing greater positive emotions after a positive event. It is important to note that this polymorphism is only one of many factors contributing to the development of these kind of outlooks/experiences. | 24690898 |
| 23-01 | CNR1 | rs806379 | Mental Health & Wellness | COGNITIVE | The endocannabinoid signaling system (ECS) helps control neural development, particularly during adolescence. The ECS is vulnerable to disturbances during this time (including exposure to exogenous cannabinoids) and disturbances may lead to impairments in self control. In one study of communities at risk for extra stressors, this polymorphism was linked to adolescent impulsivity following early psychosocial adversity. In particular, early adversity is | 24980155 |

TABLE 10-continued

Single-nucleotide polymorphisms (SNPs), endocannabinoid genotype, and potential formulation.

| | | | | | | |
|---|---|---|---|---|---|---|
| | | | | | linked to enhanced impulsivity among homozygous carriers of the rs806379 A and the rs1049353 T allele when compared to homozygous carriers of the respective major allele. It is important to note that this polymorphism is only one of many contributing factors to this profile. | |
| 24-01 | CNR2 | rs2501432 | Mental Health & Wellness | COGNITIVE | In a Japanese study that compared both humans, this polymorphism was associated with higher vulnerability to depression. It is important to note that this is only one of many factors if and how you may experience depressive behaviors. | 18991891 |
| 25-01 | CNR2 | rs41311993 | Mental Health & Wellness | COGNITIVE | Tliis polymorphism was significantly associated with the risk for developing bipolar disorder (BD). It is important to note that this is only one of many factors linked to tliis profile. | 21658778 |
| 37-01 | FAAH | rs324420 | Mental Health & Wellness | COGNITIVE | This polymorphism was associated with threat-related anxiety, reward-related impulsivity, and activation of associated brain areas (the amygdala and ventral striatum, respectively). It is important to note that this polymorphism is only one of many contributing factors to tliis profile. | 19103437 |
| 38-01 | FAAH | rs324420 | Mental Health & Wellness | REST | This polymorphism was associated with poorer sleep quality among young cannabis users. Depressive symptoms were identified as a possible link between this polymorphism and poor sleep quality. It is important to note that this polymorphism is only one of many contributing factors to this profile. | 27074158 |
| 1-01-AFMLG | ABCB1 | rs1045642 | Drug Dependence | RESPONSE | This polymorphism was associated with the risk of cannabis dependence. This may be due to effects on brain penetration of THC or effects on elimination of THC from the body. It is important to note that this polymorphism is only one of many contributing factors to developing cannabis dependence. | 19625010 |
| 10-01-2AFML | CNR1 | rs1049353 | Drug Dependence | RESPONSE | This polymorphism had a weak trend towards association with cannabis dependence symptoms in young adults. This research was also carried out in a specific population of youth with polysubstance dependence and conduct problems, and thus the results may not be generalizable to other groups of youth or adults. It is important to note that this is only one of many factors | 19443135 |

TABLE 10-continued

Single-nucleotide polymorphisms (SNPs), endocannabinoid genotype, and potential formulation.

| | | | | | | |
|---|---|---|---|---|---|---|
| 18-01-AFMG | CNR1 | rs2023239 | Drug Dependence | RESPONSE | determining whether and how cannabis dependence occur. One research study linked this polymorphism to craving for cannabis after 5 days of abstinence in daily cannabis smokers. Craving for a drug is a warning sign for psychological dependence. It is important to note that this polymorphism is only one of many contributing factors to dependency issues. | 18705688 |
| 22-01 | CNR1 | rs806379 | Drag Dependence | COGNITIVE | Nicotine withdrawal can cause cognitive disruption, which is partially mediated by the endocannabinoid system. This polymorphism was associated with the degree of cognitive disruption during nicotine withdrawal. Current research suggests potential efficacy of a pharmacotherapy approach for smoking cessation among individuals who exhibit greater nicotine withdrawal-related cognitive disruption. | 27453054 |
| 35-01 | DRD2 | rsl800497 | Drug Dependence | COGNITIVE | Tliis polymorphism was associated with the risk of cannabis dependence. There was also an interaction noted with the CNR1 rs1049353 polymorphism. It is important to note that this polymorphism is only one of many contributing factors to this profile. | 26833047; 22536882 |
| 36-01 | FAAH | rs324420 | Drug Dependence | RESPONSE | This polymorphism was associated with risky alcohol use. which is a precursor to more significant dependence on alcohol. It is important to note that this polymorphism is only one of many contributing factors to this profile. | 24407958 |
| 43-01 | MGLL | rs604300 | Drug Dependence | RESPONSE | This polymorphism was associated with cannabis dependence in a maimer that depended on the presence of early childhood abuse. It is important to note that this polymorphism is only one of many contributing factors to this profile. | 26595473 |
| 44-01 | NCAM1 | rs4471463 | Drug Dependence | RESPONSE | This polymorphism was associated with lifetime use of cannabis. The specific outcome of this study was whether the subjects had ever tried cannabis or had never tried it. Although further study is needed, this polymorphism could also be associated with cannabis dependence. It is important to note that this polymorphism is only one of many contributing factors to this profile. | 27023175 |
| 45-01 | NRG1 | rsl7664708 | Drug Dependence | RESPONSE | This polymorphism was associated with the risk of cannabis dependence in a group of African Americans. This finding was not replicated in European | 22520967 |

TABLE 10-continued

Single-nucleotide polymorphisms (SNPs), endocannabinoid genotype, and potential formulation.

| | | | | | | |
|---|---|---|---|---|---|---|
| 48-01 | OPRM1 | rs1799971 | Drug Dependence | RESPONSE | Americans. It is important to note that this polymorphism is only one of many contributing factors to this profile.<br>This polymorphism was associated with a general risk of substance abuse, including cannabis dependence. It is important to note that this polymorphism is only one of many contributing factors to this profile. | 26392368 |
| 49-01 | PENK | rs2609997 | Drug Dependence | RESPONSE | This polymorphism was associated with cannabis dependence. This risk was modified by the neuroticism personality trait, which describes a person's propensity for experiencing negative emotions. (Limitations of the research include that the sample was drawn from a population without significant psychiatric comorbidity). It is important to note that this polymorphism is only one of many contributing factors to this profile. | 22745721 |

| SNIP I.D. | Gene | Major Allele | Minor Allele | Suggestion - Homozygous MAJOR Allele | Suggestion - Heterozygous | Suggestion - Homozygous MINOR Allele |
|---|---|---|---|---|---|---|
| 2-01-AFMLG | ABCB1 | C | T | Homozygous MAJOR Alleles (C/C) Research indicates you may have higher THC levels in your blood after consuming THC relative to other genotypes. | Heterozygous Alleles (C/T) Research indicates you may have 2-fold lower THC levels in your blood after consuming THC relative to people with the most common genotype. | Homozygous MINOR Alleles (T/T) Research indicates you may have 2-fold lower blood THC levels after consuming THC relative to people with the most common genotype. |
| 3-01-A | AKT1 | C | T | Homozygous MAJOR Alleles (C/C)Research indicates you may have an increased risk of experiencing acute psychotomimetic effects after consuming THC. Your risk is highest if you also carry an SLCA6 3' UTR VNTR 9R allele. Caution and consultation with a licensed medical professional who focuses on THC/CBD titration/adjustments and cessation.is recommended to assess your risks. | Heterozygous Alleles (C/T)Research indicates you may have a lower risk of experiencing acute psychotomimetic effects after consuming THC. | Homozygous MINOR Alleles (T/T)Research indicates you may have a lower risk of experiencing acute psychotomimetic effects after consuming THC. |
| 4-01-A | AKT1 | C | T | Homozygous MAJOR Alleles (C/C) Research indicates you may be less likely to develop coordination impairment after consuming THC. | Heterozygous Alleles (C/T) Research indicates you may be less likely to develop coordination impairment after consuming THC. | Homozygous MINOR Alleles (T/T) Research indicates you may develop coordination impairment after consuming THC. Avoid using alcohol when consuming THC. Careful titration of dose under supervision a licensed medical professional who focuses on THC/CBD |

TABLE 10-continued

Single-nucleotide polymorphisms (SNPs), endocannabinoid genotype, and potential formulation.

| | | | | | | |
|---|---|---|---|---|---|---|
| | | | | | | titration/adjustments and cessation. |
| 5-01-2AL | AKT1 | T | C | Homozygous MAJOR Alleles (T/T)You may have a lower risk of developing a psychotic disorder with cannabis use relative to people with other genotypes. | Heterozygous Alleles (T/C)You may have an increased likelihood of a psychotic disorder with cannabis use. This risk is especially elevated in daily cannabis users. Caution is warranted. Consultation with a licensed medical professional who focuses on THC & CBD titration is recommended. | Homozygous MINOR Alleles (C/C)You may have an increased likelihood of a psychotic disorder with cannabis use. This risk may be especially elevated in daily cannabis users. Caution is warranted. Consultation with a licensed medical professional who focuses on THC/CBD titration is recommended. |
| 6-01-2AL | AKT1 | T | C | Homozygous MAJOR Alleles (T/T) You may have a lower risk of memory and attention impairments after consuming THC. | Heterozygous Alleles (T/C) You may have a lower risk of memory and attention impairments after consuming THC. | Homozygous MINOR Alleles (C/C) You may be at a higher risk of impairments in memory and attention after consuming THC relative to people with other genotypes. Responsible use is warranted. |
| 7-01-2AL | AKT1 | T | C | Homozygous MAJOR Alleles (T/T)Research indicates you may have a lower risk of experiencing acute psychotomimetic effects (psychosis-like) after consuming THC. | Heterozygous Alleles (TC)You may have an increased risk of experiencing acute psychotomimetic effects after consuming THC. Caution and consultation with a specialist are recommended to assess your risks. | Homozygous MINOR Alleles (C/C)You may have an increased risk of experiencing acute psychotomimetic effects (psychosis-like) after consuming THC. Caution and consultation with a specialist are recommended to assess your risks. |
| 8-01-2AL | AKT1 | T | C | Homozygous MAJOR Alleles (T/T) Research indicates that THC may not increase your risk of developing psychosis relative to other genotypes. | Heterozygous Alleles (T/C) If you are predisposed to developing psychosis, THC may increase your risk. The risk is highest with more frequent use of THC and in those who also carry a DRD2 rs107650 A allele. Caution and consultation with a licensed medical professional who focuses on THC & CBD titration is recommended to assess your risks. | Homozygous MINOR Alleles (C/C) If you are predisposed to developing psychosis, THC may increase your risk. The risk is highest with more frequent use of THC and in those who also carry a DRD2 rs107650 A allele. Caution and consultation with a licensed medical professional who focuses on THC & CBD titration is recommended to assess your risks. |
| 9-01-ALG | BDNF | G | A | Homozygous MAJOR Alleles (G/G)Research indicates If you are female who is predisposed to developing psychosis, cannabis use may not result in an earlier age of onset of psychosis. | Heterozygous Alleles (G/A)If you are female who is predisposed to developing psychosis, cannabis use may result in a significantly earlier age of onset of psychosis. The effect of cannabis depends on the extent of cannabis use and the age at which you start using it. Use with caution and consult a | Homozygous MINOR Alleles (A/A)If you are female who is predisposed to developing psychosis, cannabis use may result in a significantly earlier age of onset of psychosis. The effect of cannabis depends on the extent of cannabis use and the age at which you start using it. Use with caution and consult a specialist for a dose titration. |

TABLE 10-continued

Single-nucleotide polymorphisms (SNPs), endocannabinoid genotype, and potential formulation.

| | | | | | | |
|---|---|---|---|---|---|---|
| | CNR1 | | | Based on your TAG haplotype of ACA, you may have a higher risk of experiencing acute psychomimetic effects after consumption of THC. Do not consume alcohol and other substances in parallel with THC use. Consult a specialist for a dose titration. | specialist for a dose titration. Based on your TAG haplotype of AAA, you may have a lower risk of experiencing acute psychomimetic effects after consumption of THC. | |
| 16-01-2AFML | CNR1 | C | T | Homozygous MAJOR Alleles (C/C)You may have greater ability in sustained attention relative to people with other genotypes. | Heterozygous Alleles (C/T)You may have an elevated risk of impairments in sustained attention with cannabis use relative to people with the most common genotype. Consume responsibly. | Homozygous MINOR Alleles (T/T)You may have an elevated risk of impairments in sustained attention with cannabis use relative to people with the most common genotype. Consume responsibly. |
| 17-01-AFM | CNR1 | T | C | Homozygous MAJOR Alleles (T/T) You may be less likely to experience working memory impairments after use of THC. | Heterozygous Alleles (T/C) You may be more likely to experience working memory impairments after use of THC. Careful dose titration is warranted. Please consult a specialist. | Homozygous MINOR Alleles (C/C) You may be more likely to experience working memory impairments after use of THC. Careful dose titration is warranted. Please consult a specialist. |
| 26-01-2 | COMT | G | A | Homozygous MAJOR Alleles (G/G) You may be more likely to experience psychotomimetic effects after consuming THC. Although there are other predisposing factors, caution is warranted upon THC consumption. | Heterozygous Alleles (G/A) You may be more likely to experience psychotomimetic effects after consuming THC. Although there are other predisposing factors, caution is warranted upon THC consumption. | Homozygous MINOR Alleles (A/A) You may be less likely to experience psychotomimetic effects after consuming THC relative to people with other genotypes. However, there are other predisposing factors. |
| 27-01-2 | COMT | G | A | Homozygous MAJOR Alleles (G/G)You may be at increased risk of brain volume changes following cannabis use that are linked to alterations in emotions and memory. | Heterozygous Alleles (G/A)You may be at increased risk of brain volume changes following cannabis use that are linked to alterations in emotions and memory. | Homozygous MINOR Alleles (AA)You may have a decreased risk of brain volume changes following cannabis use that are linked to alterations in emotions and memory. |
| 28-01-2 | COMT | G | A | Homozygous MAJOR Alleles (G/G) You may experience greater cognitive impairment after consuming THC relative to people with other genotypes. Caution and careful titration of THC is highly recommended. | Heterozygous Alleles (G/A) You may experience greater cognitive impairment after consuming THC relative to people with the AA genotype. Caution and careful titration of THC is highly recommended. | Homozygous MINOR Alleles (A/A) You may experience less cognitive impairment after consuming THC relative to people with other genotypes. Caution and careful titration of THC is still recommended. |
| 29-01-2 | COMT | G | A | Homozygous MAJOR Alleles (G/G)You may have a higher risk for dependence on cannabis and associated cravings relative to other genoty pes. Caution and consultation with a specialist is recommended. | Heterozygous Alleles (G/A)You may have a relatively lower risk to develop dependence on cannabis relative to people with the most common genotype. | Homozygous MINOR Alleles (A/A)You may have a relatively lower risk to develop dependence on cannabis relative to people with the most common genotype. |

TABLE 10-continued

Single-nucleotide polymorphisms (SNPs), endocannabinoid genotype, and potential formulation.

| | | | | | | |
|---|---|---|---|---|---|---|
| 30-01-2AFMLG | CYP2C9 | A | C | Homozy gous MAJOR Alleles (A/A) As you do not have a version of CYP2C9 with reduced activity, you can start oral THC at a typical dose. However, this is not the only factor affecting sensitivity to THC and careful dose titration is still recommended. | Heterozygous Alleles (A/C) You may feel the effects of oral THC more strongly or find that the effects last longer relative to people with the most common genotype. It is recommended that the first time you use oral THC, you start at 60% of the standard dose. No change in THC dose is needed for pulmonary administration. | Homozygous MINOR Alleles (C/C) You may feel the effects of oral THC more strongly or find that the effects last longer relative to people with the most common genotype. It is recommended that the first time you use oral THC, you start at 30% of the standard dose. No change in THC dose is needed for pulmonary administration. |
| 31-01 | CYP3A4 | C | T | Homozygous MAJOR Alleles (C/C)As you have the ty pical version of CYP3A4, you may start oral THC or CBD at a normal dose. However, this is not the only factor affecting sensitivitity to THC. | Heterozygous Alleles (C/T)You may feel the effects of oral THC more strongly or find that the effects last longer relative to other people. It is recommended that the first time you use oral THC. you start at 75% of the standard dose. No change in THC dose is needed for pulmonary administration. | Homozygous MINOR Alleles (T/T)You may feel the effects of oral THC more strongly or find that the effects last longer relative to other people. It is recommended that the first time you use oral THC. you start at 50% of the standard dose. No change in dose is needed for pulmonary administration. |
| 32-01 | DAT1 | | | You may be at risk for reduced hippocampal volume with cannabis use. This could lead to long- and short-term memory impairments and altered emotions. Responsible use and consultation with a specialist is warranted. | This genotype was not associated with reduced hippocampal volume in cannabis users. | This genotype was not associated with reduced hippocampal volume in cannabis users. |
| 33-01 | DBH | C | T | Homozygous MAJOR Alleles (C/C)This genotype was not associated with increased impulsivity after cannabis use. | Heterozygous Alleles (C/T)You may be more likely to act impulsively after consuming cannabis. Responsible use is warranted. | Homozygous MINOR Alleles (T/T)You may be more likely to act impulsively after consuming cannabis. Responsible use is warranted. |
| 34-01-2AFMLG | DRD2 | C | A | Homozygous MAJOR Alleles (C/C) THC may not increase your risk of developing psychosis relative to other genotypes. | Heterozygous Alleles (A/C) If you are predisposed to developing psychosis, THC may increase your risk. The risk is highest with more frequent use of THC and in those who also carry an AKT1 rs2494732 C allele. Caution and consultation with a specialist are recommended to assess your risks. | Homozygous MINOR Alleles (A/A) If you are predisposed to developing psychosis, THC may increase your risk. The risk is highest with more frequent use of THC and in those who also carry an AKT1 rs2494732 C allele. Caution and consultation with a specialist are recommended to assess your risks. |
| 41-01 | FAAH | C | A | Homozygous MAJOR Alleles (C/C) You may be more likely relative to other genotypes to experience decreased white matter integrity with cannabis use at a young age. Careful dose titration is warranted. Please consult a specialist. | Heterozygous Alleles (C/A) You may have less risk for decreased white matter integrity with cannabis use relative. Cautious use is warranted. | Homozygous MINOR Alleles (A/A) You may have less risk for decreased white matter integrity with cannabis use. Cautious use is warranted. |

TABLE 10-continued

Single-nucleotide polymorphisms (SNPs), endocannabinoid genotype, and potential formulation.

| | | | | | | |
|---|---|---|---|---|---|---|
| 42-01 | MAPK14 | A | G | Homozygous MAJOR Alleles (A/A) You may have a higher risk of decreased white matter brain volume from cannabis use. This could impair your cognition. Use with caution and consult a specialist for a dose titration. | Heterozygous Alleles (A/G) Your genotype may not confer risk of decreased white matter volume from cannabis use. Cautious use is warranted. | Homozygous MINOR Alleles (G/G) Your genotype may not confer risk of decreased white matter volume from cannabis use. Cautious use is warranted. |
| 46-01 | NRG1 | T | C | Homozygous MAJOR Alleles (T/T) You may have a lower risk of experiencing psychomimetic effects following cannabis use relative to people with the (T/T) genotype. | Heterozygous Alleles (T/C) You may have a lower risk of experiencing psychomimetic effects following cannabis. | Homozygous MINOR Alleles (C/C) You may have a higher risk of experiencing psychomimetic effects following cannabis use relative to people with the other genotypes. Consume responsibly and consult a specialist for guidance. |
| 47-01 | NRG1 | C | A | Homozygous MAJOR Alleles (C/C) You may be less likely to develop psychomimetic effects after cannabis consumption relative to people with other genotypes. Responsible consumption and a titration with a help of a specialist is warranted. | Heterozygous Alleles (C/A) You may be more likely to develop psychomimetic effects after cannabis consumption. Responsible consumption and a titration with a help of a specialist is warranted. | Homozygous MINOR Alleles (A/A) You may be more likely to develop psychomimetic effects after cannabis consumption. Responsible consumption and a titration with a help of a specialist is warranted. |
| 50-01 | SLC6A3 | 10R | 9R | You may have a lower risk of experiencing acute psychotomimetic effects after consuming THC. | You may have an increased risk of experiencing acute psychotomimetic effects after consuming THC. Your risk is highest if you also have an AKT1 C/C genotype. Caution and consultation with a specialist are recommended to assess your risks and prevent them. | You may have an increased risk of experiencing acute psychotomimetic effects after consuming THC. Your risk is highest if you also have an AKT1 C/C genotype. Caution and consultation with a specialist are recommended to assess your risks and prevent them. |
| 51-01 | SLC6A3 | 10R | 9R | You may have a lower risk of impulsivity after consuming cannabis compared to other genotypes. | You may have a higher risk of impulsivity after consuming cannabis relative to the most common genotype. | You may have a higher risk of impulsivity after consuming cannabis relative to the most common genotype. |
| 52-01 | SLC6A4 | L' | S' | Adolescents may be at increased risk of developing anxiety following cannabis use, but this genotype was not associated with extra risk. Cannabis should only be used responsibly once legal age is attained. | Adolescents with this genotype may be at increased risk of developing anxiety following cannabis use. Cannabis should only be used responsibly once legal age is attained. | Adolescents with this genotype may be at increased risk of developing anxiety following cannabis use. Cannabis should only be used responsibly once legal age is attained. |
| 53-01 | SLC6A4 | L' | S' | Your genotype was not associated with heightened risk of psychotomimetic symptoms in patients with bipolar disorder. | Please be advised that if you or your close blood related relatives have bipolar disorder, you may be at a higher risk of psychotic effects with cannabis consumption\. Careful titration of THC dose and a consultation with a specialist is suggested. | Please be advised that if you or your close blood related relatives have bipolar disorder, you may be at a higher risk of psychotic effects with cannabis consumption\. Careful titration of THC dose and a consultation with a specialist is suggested. |

TABLE 10-continued

Single-nucleotide polymorphisms (SNPs), endocannabinoid genotype, and potential formulation.

| | | | | | | |
|---|---|---|---|---|---|---|
| 54-01 | SLC6A4 | L' | S' | You may be less likely to experience a decrease in decision making ability as a result of using cannabis. | You may be less likely to experience a decrease in decision making ability as a result of using cannabis. | You may be more likely to experience a decrease in decision making ability as a result of using cannabis compared to people of other genotypes. Caution is warranted. |
| | CNR1 | | | Based on your genotype of <10/<10, you may have a lower risk of developing IBS relative to people of other genotypes. | Based on your genotype of <10/>10, you may have an elevated risk of developing IBS. A specialist should be consulted for THC dose titration. | Based on your genotype of >10/>10, you may have an elevated risk of developing IBS. If you have IBS or develop it in the future, you may have more severe symptoms than patients with a different genotype. A specialist should be consulted for THC dose titration. |
| 20-01-AFM | CNR1 | T | C | Homozygous MAJOR Alleles (T/T)You may be more likely to experience headache with nausea after a stressful event in your life. Use THC responsibly and consult a specialist to titrate a dose appropriately to your condition. | Heterozygous Alleles (T/C)This genotype does not appear to confer greater risk of experiencing headache with nausea after recent stressful life events. | Homozygous MINOR Alleles (C/C)This genotype does not appear to confer greater risk of experiencing headache with nausea after recent stressful life events. |
| 39-01 | FAAH | C | A | Homozygous MAJOR Alleles (C/C) You may have higher cold pain sensitivity and more need for analgesia during periods of acute pain, such as after an operation. | Heterozygous Alleles (C/A) You may have higher cold pain sensitivity and more need for analgesia during periods of acute pain, such as after an operation. | Homozygous MINOR Alleles (A/A) You may have significantly lower cold pain sensitivity and less need for analgesia during periods of acute pain, such as after an operation. |
| 40-01 | FAAH | C | A | Homozygous MAJOR Alleles (C/C) You may have a lower risk experiencing side effects from opioids relative to people with other genotypes. | Heterozygous Alleles (C/A) You may have a higher risk of experiencing side effects from opioids relative to people with the most common genotype. If you will be receiving opioids, consider informing your physician of a potential predisposition to respiratory depression and nausea/vomiting. | Homozygous MINOR Alleles (A/A) You may have a higher risk of experiencing side effects from opioids relative to people with the most common genotype. If you will be receiving opioids, consider informing your physician of a potential predisposition to respiratory depression and nausea/vomiting. |
| 11-01-2AFML | CNR1 | C | T | Homozygous MAJOR Alleles (C/C)Research indicates you that if you have experienced childhood physical abuse, you may have increased risk of posttraumatic threat symptoms relative to people with other genotypes. Please consult a specialist if symptoms are present. | Heterozygous Alleles (C/T)If you have experienced childhood physical abuse, you may have a lower risk of posttraumatic threat symptoms relative to people with the most common genotype. | Homozygous MINOR Alleles (T/T)If you have experienced childhood physical abuse, you may have a lower risk of posttraumatic threat symptoms relative to people with the most common genotype. |
| 12-01-2AFML | CNR1 | C | T | Homozygous MAJOR Alleles (C/C) Research indicates that if you are a male patient with depression, you may respond better to treatment with | Heterozygous Alleles (C/T) Research indicates that if you are a male patient with depression, you may have a decreased | Homozygous MINOR Alleles (T/T) Research indicates that if you are a male patient with depression, you may have decreased likelihood of responding |

TABLE 10-continued

Single-nucleotide polymorphisms (SNPs), endocannabinoid genotype, and potential formulation.

| | | | | | | |
|---|---|---|---|---|---|---|
| | | | | antidepressants such as citalopram. Consult a specialist prior to cannabinoid use or making any change in antidepressant treatment. | likelihood of responding to antidepressants such as citalopram/Celexa*. Consult a specialist prior to cannabinoid use or making any change in antidepressant treatment. | to antidepressants such as citalopram/Celexa. Consult a specialist prior to cannabinoid use or making any change in antidepressant treatment. |
| 13-01-2AFML | CNR1 | C | T | Homozygous MAJOR Alleles (C/C)Research indicates adolescents who experienced early psychosocial adversity may not have an elevated risk of impulsive behavior. | Heterozygous Alleles (C/T)Research indicates adolescents who experienced early psychosocial adversity may have a slightly higher of risk of impulsive behavior. Consult a specialist for cannabinoid dose titration. | Homozygous MINOR Alleles (T/T)Research indicates that adolescents who experienced early psychosocial adversity may have a higher of risk of impulsive behavior. Consult a specialist for cannabinoid dose titration. |
| 14-01-2AFML | CNR1 | C | T | Homozygous MAJOR Alleles (C/C) You may have lower resting state EEG theta power. This may be correlated with lower working memory performance. | Heterozygous Alleles (C/T) Research indicates you may have a higher resting state EEG theta power relative to the most common genotype. This may be correlated with better working memory. | Homozygous MINOR Alleles (T/T) Research indicates you may have a higher resting state EEG theta power relative to the most common genotype. This may be correlated with better working memory. |
| 15-01-2AFML | CNR1 | C | T | Homozygous MAJOR Alleles (C/C)You may have greater amygdala and insula activation upon viewing angry faces or similar stimuli. | Heterozygous Alleles (C/T)You may have less amygdala and insula activation upon viewing angry faces or similar stimuli. | Homozygous MINOR Alleles (T/T)You may have less amygdala activation upon viewing angry faces similar stimuli. |
| 19-01-AFMG | CNR1 | T | c | Homozygous MAJOR Alleles (T/T) You may be more likely to experience depression. Use THC with caution as it could potentiate your symptoms Consult a specialist for a careful dose titration / adjustment. | Heterozygous Alleles (T/C) You may be less likely to experience depression relative to people with the most common genotype. Caution with use of THC is still recommended. | Homozygous MINOR Alleles (C/C) You may be less likely to experience depression relative to people with the most common genotype. Caution with use of THC is still recommended. |
| 21-01-AFLG | CNR1 | T | C | Homozygous MAJOR Alleles (T/T)Research indicates that you may experience more overall happiness in life and experience greater positive emotions after a positive event. In one study, C allele of CNR1 was significantly associated with an increased subjective happiness level noting that long term sociological factors affect the momentary emotional state. | Heterozygous Alleles (T/C)Research indicates that you may experience more overall happiness in life and experience greater positive emotions after a positive event, noting that long term sociological factors affect the momentary emotional state. | Homozygous MINOR Alleles (C/C)Research indicates you may experience more overall happiness in life and experience greater positive emotions after a positive event, noting that long term sociological factors affect the momentary emotional state. |
| 23-01 | CNR1 | A | T | Homozygous MAJOR Alleles (A/A)Research indicates that adolescents who experienced early psychosocial adversity may have a higher risk of impulsive behavior. Consult a specialist for | Heterozygous Alleles (A/T)Research indicates that adolescents who have experienced early psychosocial adversity may have a slightly higher of risk | Homozygous MINOR Alleles (T/T)Research indicates that adolescents who experienced early psychosocial adversity may not have an elevated risk of impulsive behavior. |

TABLE 10-continued

Single-nucleotide polymorphisms (SNPs), endocannabinoid genotype, and potential formulation.

| | | | | cannabinoid dose titration. | of impulsive behavior. Consult a specialist for cannabinoid dose titration. | |
|---|---|---|---|---|---|---|
| 24-01 | CNR2 | C | T | Homozygous MAJOR Alleles (C/C) Your risk of depression may be lower relative to people with other genotypes. This polymorphism is only factor in the risk for developing depression. | Heterozygous Alleles (C/T) You may have a higher than average risk of developing depression. Watch for symptoms of depression and consider consulting with a specialist if these symptoms are interfering with your daily life. | Homozygous MINOR Alleles (T/T) You may have a higher than average risk of developing depression. Watch for symptoms of depression and consider consulting with a specialist if these symptoms are interfering with your daily life. |
| 25-01 | CNR2 | G | T | Homozygous MAJOR Alleles (G/G)You may have a lower risk of developing bipolar disorder relative to people of other genotypes. | Heterozygous Alleles (G/T)You may have a higher risk of developing bipolar disorder relative to people of the most common genotype. | Homozygous MINOR Alleles (T/T)You may have a higher risk of developing bipolar disorder relative to people of the most common genotype. |
| 37-01 | FAAH | C | A | Homozygous MAJOR Alleles (C/C) You may have greater anxiety (and associated activation of the amygdala) in a threatening situation relative to other genotypes. However, you may have decreased reward-related impulsivity. | Heterozygous Alleles (C/A) You may have reduced anxiety (and associated activation of the amygdala) in a threatening situation relative to the most common genotype. Hoyvever, you may have increased reyvard-related impulsivity (and associated activation of the ventral striatum). | Homozygous MINOR Alleles (A/A) You may have reduced anxiety (and associated activation of the amygdala) in a threatening situation relative to the most common genotype. Hoyvever, you may have increased reward-related impulsivity (and associated activation of the ventral striatum). |
| 38-01 | FAAH | C | A | Homozygous MAJOR Alleles (C/C) You may be at increased risk of poor sleep quality. Consume THC responsibly and consult a specialist for an optimal dose titration. | Heterozygous Alleles (C/A) This polymorphism does not appear to increase your risk of poor sleep. | Homozygous MINOR Alleles (A/A) This polymorphism does not appear to increase your risk of poor sleep. |
| 1-01-AFMLG | ABCB1 | C | T | Homozygous MAJOR Alleles (C/C)Research indicates you may have a higher risk of cannabis dependence. Consider consulting with a medical professional with experience in THC & CBD dose titration. | Heterozygous Alleles (C/T)Research indicates you may have a higher risk of cannabis dependence. Consider consulting with a medical professional with experience in THC & CBD dose titration. | Homozygous MINOR Alleles (T/T) Research indicates you may have an even less cannabis dependence relative to other genotypes combinations. Your genotype at this polymorphism does not suggest a specific type of cannabis product you should consume. Your choice of cannabis product can be driven by any symptoms you may have. However, thoroughly check all polymorphisms in this report for areas where you may have heightened risks. |
| 10-01-2AFML | CNR1 | C | T | Homozygous MAJOR Alleles (C/C) You may have a higher risk of developing symptoms of cannabis dependence. Please | Heterozygous Alleles (C/T) You may have a higher risk of developing symptoms of cannabis | Homozygous MINOR Alleles (T/T) You may have a lower risk of developing symptoms of cannabis dependence relative to |

TABLE 10-continued

Single-nucleotide polymorphisms (SNPs), endocannabinoid genotype, and potential formulation.

| | | | | | | |
|---|---|---|---|---|---|---|
| | | | | consume responsibly and consult with a specialist for guidance. | dependence. Please consume responsibly and consult with a specialist for guidance. | people with the most common genotype. |
| 18-01-AFMG | CNR1 | T | C | Homozygous MAJOR Alleles (T/T) Research indicates you that if you are a regular cannabis user, you may experience less cravings and withdrawal after stopping relative to the other genotypes. If there are indications you are dependent on cannabis and have trouble stopping, it is recommended that you consult with a licensed medical professional who focuses on THC/CBD titration and cessation. | Heterozygous Alleles (T/C) Research indicates you if you are a regular cannabis user, you may experience stronger cravings and withdrawal after stopping relative to people with the most common genotype. If you feel that you are dependent on cannabis and have trouble stopping, it is recommended that you consult with a licensed medical professional who focuses on THC/CBD titration/adjustments and cessation. | Homozygous MINOR Alleles (C/C) Research indicates you that if you are a regular cannabis user, you may experience stronger cravings and withdrawal after stopping relative to people with the most common genotype. If you feel that you are dependent on cannabis and have trouble stopping, it is recommended that you consult with a licensed medical professional who focuses on THC & CBD titration and cessation. |
| 22-01 | CNR1 | A | T | Homozygous MAJOR Alleles (A/A) Research indicates that based on your genotype, you may exhibit greater nicotine withdrawal-related cognitive dismption. | Heterozygous Alleles (A/T) Research indicates that based on your genotype, you may exhibit less nicotine withdrawal-related cognitive dismption. | Homozygous MINOR Alleles (T/T) Research indicates that based on your genotype, you may exhibit less nicotine withdrawal-related cognitive dismption. |
| 35-01 | DRD2 | G | A | Homozy gous MAJOR Alleles (G/G) You may have decreased likelihood of developing cannabis dependence. | Heterozygous Alleles (G/A) You may have decreased likelihood of developing cannabis dependence. | Homozygous MINOR Alleles (A/A) You may have a greater likelihood of developing cannabis dependence, with associated cravings and mood changes. Avoid mixing alcohol and cannabis. Consult a specialist for dose titration. |
| 36-01 | FAAH | C | A | Homozy gous MAJOR Alleles (C/C) You may be significantly more likely to use alcohol in a risky fashion. Use THC responsibly and don't combine with alcohol use. | Heterozygous Alleles (C/A) You may have a lower risk of engaging in risky alcohol use. | Homozygous MINOR Alleles (A/A) You may have a lower risk of engaging in risky alcohol use. |
| 43-01 | MGLL | G | A | Homozygous MAJOR Alleles (G/G) Although your genotype may be protective against cannabis dependence, this protective effect appears to be absent if you have experienced early childhood stress or abuse. Cautious use is warranted. Consult a specialist for a dose titration. | Heterozygous Alleles (G/A) You may have increased risk of cannabis dependence independent of early childhood stress or abuse. Caution and responsible use is warranted. | Homozygous MINOR Alleles (A/A) You may have increased risk of cannabis dependence independent of early childhood stress or abuse. Caution and responsible use is warranted. |
| 44-01 | NCAM1 | T | C | Homozygous MAJOR Alleles (T/T) You may be less likely to ever consume cannabis relative to people with other genotypes. | Heterozygous Alleles (T/C) You may have a greater likelihood of using cannabis relative to people with the most common genotype. | Homozygous MINOR Alleles (C/C) You may have a greater likelihood of using cannabis relative to people with the most common genotype. |

TABLE 10-continued

Single-nucleotide polymorphisms (SNPs), endocannabinoid genotype, and potential formulation.

| | | | | | | Although not yet directly studied, this may extend to a greater likelihood of cannabis dependence. Consume responsibly. | Although not yet directly studied, this may extend to a greater likelihood of cannabis dependence. Consume responsibly. |
|---|---|---|---|---|---|---|---|
| 45-01 | NRG1 | C | T | | Homozygous MAJOR Alleles (C/C) If you are African American, you may have a lower risk of cannabis dependence in comparison to the other genotypes. | Heterozygous Alleles (C/T) If you are African American, you may have a higher risk of cannabis dependence relative to the most common genotype. | Homozygous MINOR Alleles (T/T) If you are African American, you may have a higher risk of cannabis dependence relative to the most common genotype. |
| 48-01 | OPRM1 | A | G | | Homozygous MAJOR Alleles (A/A) You may have a slightly higher risk of substance abuse, including cannabis dependence, relative to the other genotypes. | Heterozygous Alleles (A/G) You may have a slightly lower risk of substance abuse, including cannabis dependence, relative to the most common genotype. | Homozygous MINOR Alleles (G/G) You may have a slightly lower risk of substance abuse, including cannabis dependence, relative to the most common genotype. |
| 49-01 | PENK | T | C | | Homozygous MAJOR Alleles (T/T)You may be less likely to develop symptoms of cannabis dependence relative to people with other genotypes. | Heterozygous Alleles (T/C)You may be more likely to develop symptoms of cannabis dependence relative to people with the most common genotype. This risk may be increased further if you have high levels of neuroticism. Consume THC responsibly and consult a specialist for guidance. | Homozygous MINOR Alleles (C/C)You may be more likely to develop symptoms of cannabis dependence relative to people with the most common genotype. This risk may be increased further if you have high levels of neuroticism. Consume THC responsibly and consult a specialist for guidance. |

All-allele disclaimer: Your choice of cannabis product can be driven by any symptoms you may have. However, thoroughly check all polymorphisms in this report for areas where you may have heightened risks.
Non-risk Allele disclaimer: Your genotype at this polymorphism does not suggest a specific type of cannabis.

What is claimed is:

1. A formulation comprising:
   a cannabidiol (CBD) and a tetrahydrocannabinol (THC), wherein the formulation has a CBD:THC ratio from about 1:1 to about 1:5;
   a primary terpene of myrcene at about 3-5%; and
   a secondary terpene of linalool at about 1-5%.

2. The formulation of claim 1, comprising branched-chain amino acids, L-glutamine, piperine, magnesium stearate, MCC, and silicon dioxide, wherein the CBD:THC ratio is about 1:2.

3. The formulation of claim 1, wherein the formulation comprises less than about 25%, 20%, 15%, 10%, 5%, 4%, 3%, or 2% terpenes.

4. The formulation of claim 1, wherein the formulation further comprises cannabigerol (CBG), cannabinol (CBN), cannabidvarin (CBDV), cannabidiolic acid (CBDA), tetrahydrocannabinolic acid (THCA), or tetrahydrocannabivarin (THCV).

5. The formulation of claim 1, wherein the formulation further comprises black pepper, branched-chain amino acids (BCAA), cayenne, cedarwood, chamomile, coconut oil, geranium, ginger, ginger oil, glutamine, guava, juniper berry, lavender, lemon, lemon oil, lemongrass, lime, lime oil, orange, orange oil, mango, marjoram, menthol, mint, mint oil, peppermint, peppermint oil, piperine, geranium, rosemary, sandalwood, or tangerine.

6. The formulation of claim 1, comprising 5% myrcene and 3% linalool, wherein the CBD: THC ratio is about 1:1.

7. The formulation of claim 1, further comprising terpinolene.

8. The formulation of claim 7, comprising 1-3% terpinolene.

9. The formulation of claim 1, further comprising lavender, chamomile, and sandalwood.

10. The formulation of claim 9, comprising 0.04-0.1% lavender, 0.04-0.1% chamomile, and 0.04-0.1% sandalwood.

* * * * *